United States Patent
Kil

(10) Patent No.: US 8,346,483 B2
(45) Date of Patent: Jan. 1, 2013

(54) INTERACTIVE AND AUTOMATED TISSUE IMAGE ANALYSIS WITH GLOBAL TRAINING DATABASE AND VARIABLE-ABSTRACTION PROCESSING IN CYTOLOGICAL SPECIMEN CLASSIFICATION AND LASER CAPTURE MICRODISSECTION APPLICATIONS

(75) Inventor: David H. Kil, Prospect, KY (US)

(73) Assignee: Life Technologies Corporation, Carlsbad, CA (US)

(*) Notice: Subject to any disclaimer, the term of this patent is extended or adjusted under 35 U.S.C. 154(b) by 634 days.

(21) Appl. No.: 10/662,765

(22) Filed: Sep. 15, 2003

(65) Prior Publication Data

US 2004/0093166 A1 May 13, 2004

Related U.S. Application Data

(60) Provisional application No. 60/410,433, filed on Sep. 13, 2002.

(51) Int. Cl.
  *G01N 33/48* (2006.01)
  *G01N 33/50* (2006.01)
(52) U.S. Cl. ........................................................ 702/19
(58) Field of Classification Search .................. None
  See application file for complete search history.

(56) References Cited

U.S. PATENT DOCUMENTS

| | | | |
|---|---|---|---|
| 5,037,207 A | 8/1991 | Tomei et al. | |
| 5,257,182 A | 10/1993 | Luck et al. | |
| 5,287,272 A | 2/1994 | Rutenberg et al. | |
| 5,403,735 A | 4/1995 | Maruhashi et al. | |
| 5,465,375 A | 11/1995 | Thepaut et al. | |
| 5,487,117 A | 1/1996 | Burges et al. | |
| 5,497,430 A | 3/1996 | Sadovnik et al. | |
| 5,625,705 A | 4/1997 | Recht | |
| 5,715,327 A | 2/1998 | Wilhelm et al. | |
| 5,734,735 A | 3/1998 | Coleman, Jr. | |
| 5,740,269 A | 4/1998 | Oh et al. | |
| 5,740,270 A | 4/1998 | Rutenberg et al. | |
| 5,745,601 A | 4/1998 | Lee et al. | |
| 5,767,923 A | 6/1998 | Coleman, Jr. | |
| 5,774,357 A | 6/1998 | Hoffberg et al. | |
| 5,778,108 A | 7/1998 | Coleman, Jr. | |
| 5,787,188 A | 7/1998 | Nelson et al. | |
| 5,859,699 A | 1/1999 | Baer et al. | |
| 5,867,610 A | 2/1999 | Lee | |
| 5,870,493 A | 2/1999 | Vogl et al. | |
| 5,875,108 A | 2/1999 | Hffberg et al. | |
| 5,889,880 A | 3/1999 | Doerrer et al. | |
| 5,920,360 A | 7/1999 | Coleman, Jr. | |
| 5,920,477 A | 7/1999 | Hoffberg et al. | |
| 5,939,278 A | 8/1999 | Boon et al. | |
| 5,959,697 A | 9/1999 | Coleman, Jr. | |
| 5,978,497 A | 11/1999 | Lee et al. | |
| 5,985,085 A | 11/1999 | Baer et al. | |
| 5,987,158 A | 11/1999 | Meyer et al. | |
| 5,999,634 A | 12/1999 | Abbott et al. | |
| 6,031,232 A | 2/2000 | Cohenford et al. | |
| 6,061,471 A | 5/2000 | Coleman, Jr. | |
| 6,134,354 A | 10/2000 | Lee et al. | |
| 6,146,897 A | 11/2000 | Cohenford et al. | |
| 6,148,099 A | 11/2000 | Lee et al. | |
| 6,157,446 A | 12/2000 | Baer et al. | |
| 6,181,811 B1 | 1/2001 | Kuan et al. | |
| 6,215,550 B1 | 4/2001 | Baer et al. | |
| 6,215,892 B1 | 4/2001 | Douglass et al. | |
| 6,240,209 B1 | 5/2001 | Wilcke | |
| 6,259,807 B1 | 7/2001 | Ravkin | |
| 6,327,377 B1 | 12/2001 | Rutenberg et al. | |
| 6,337,926 B2 | 1/2002 | Takahashi et al. | |
| 6,456,899 B1 * | 9/2002 | Gleason et al. | 700/212 |
| 6,469,779 B2 | 10/2002 | Baer et al. | |
| 6,495,195 B2 | 12/2002 | Baer et al. | |
| 6,512,576 B1 | 1/2003 | Baer et al. | |
| 6,569,639 B2 | 5/2003 | Liotta et al. | |
| 6,750,964 B2 * | 6/2004 | Levenson et al. | 356/326 |
| 6,757,412 B1 * | 6/2004 | Parsons et al. | 382/128 |
| 6,858,007 B1 * | 2/2005 | Akselrod et al. | 600/437 |
| 2001/0005586 A1 | 6/2001 | Palsson et al. | |
| 2002/0103512 A1 * | 8/2002 | Echauz et al. | 607/9 |
| 2003/0032082 A1 | 2/2003 | Leclere | |
| 2003/0219151 A1 * | 11/2003 | Curry et al. | 382/129 |
| 2004/0052328 A1 * | 3/2004 | Sabol et al. | 378/37 |

FOREIGN PATENT DOCUMENTS

| | | |
|---|---|---|
| DE | 196 36 074 A1 | 3/1998 |
| EP | 0 748 439 B1 | 7/1999 |
| WO | WO 01/33190 A2 | 5/2001 |
| WO | WO 02/37159 A2 | 5/2002 |

OTHER PUBLICATIONS

Anonymous "ChromaVision" website product description including Rare Cell Detection in Tissue and Rare Cell Detection in Cytospin Prep—retrieval date Jun. 21, 2004.

Pizzi, A. "Diagnostic Cytology Learning Page" http://www-ocs.colorado.edu/-metzj/pizzia/learning_page.html Written Feb. 4, 1997, Last updated Aug. 4, 1998.

Duke University,. "Evaluation of Cervical Cytology", AHCPR publication No. 99-E010, Feb. 1999.

Jarkrans, T. "Algorithms for Cell Image Analysis in Cytology and Pathology", Comprehensive Summaries of Uppsala Dissertations, 1996.

Morruzzi, J.F. et al. "Quantification and classification of human sperm morphology by computer assisted image analysis"—Fertil. Steril. vol. 50 , Issue 1 pp. 142-152, Jul. 1988.

(Continued)

*Primary Examiner* — Jason Sims

(57) ABSTRACT

A system and method for performing tissue image analysis and region of interest identification for further processing applications such as laser capture microdissection is provided. The invention provides three-stage processing with flexible state transition that allows image recognition to be performed at an appropriate level of abstraction. The three stages include processing at one or more than one of the pixel, subimage and object levels of processing. Also, the invention provides both an interactive mode and a high-throughput batch mode which employs training files generated automatically.

25 Claims, 21 Drawing Sheets

OTHER PUBLICATIONS

Perez-Sanchez, F. "Morphometric Analysis of human sperm morphology" Int J Androl vol. 17, Issue 5 pp. 248-255, Oct. 1994.

Jeyendran, R.S. "Association of the in-vitro fertilizing capacity of human spermatozoa with sperm morphology as assessed by three classification systems"—Hum Reprod vol. 1, Issue 5 pp. 305-308, Aug. 1986.

Grohs, H.K. and Husain, O.A.N. Eds.: "Automated Cervical Cancer Screening" Publisher: :Igaku-Shoin Medical Publishers, Chapter 23 pp. 305-317, 1994.

Salomie, A. et al. (2001). "Multivariate Techniques for Medical Image Segmentation," http://www.etro.vub.ac.be/members/deklerck.rudi/redimedia/segmentation/segment.htm.

Schachter, B. J. et al. (1979). "Some Experiments in Image Segmentation by Clustering of Local Feature Values", Pattern Recognition, Pergamon Press Inc., Elmsford, NY, US vol.

Jong-Min Park et al., (May 2002) "Analysis of active feature selection in optic nerve data using labeled fuzzy C-means clustering", 2002 IEEE World Congress on Computational Intelligence. 2002 IEEE International Conference on Fuzzy Systems, pp. 1580-1585 vol. 2, 2002, Piscataway, NJ, USA, IEEE, ISBN: 0-7803-7280-8.

Frosini, G. et al, (Jul. 2000). "A modified fuzzy C-means algorithm for feature selection", Peachfuzz 2000, 19th International Conference of the North American Fuzzy Information Processing Society, pp. 148-152, 2000, Piscataway, NJ, USA, IEEE, ISBN: 0-7803-6274-8.

Koperski,Interactive models for semantic labeling of satellite images,EarthObserving SystemsVII,Proceedings of the SPIE, vol. 4814,pp. 423-434 (2002) Sep. 2002.

* cited by examiner

INTERACTIVE AND AUTOMATED TISSUE IMAGE ANALYSIS WITH GLOBAL TRAINING DATABASE AND VARIABLE-ABSTRACTION PROCESSING IN CYTOLOGICAL SPECIMEN CLASSIFICATION AND LASER CAPTURE MICRODISSECTION APPLICATIONS

CROSS-REFERENCE TO RELATED APPLICATIONS

This application claims priority to U.S. Provisional Application Ser. No. 60/410,433, entitled "INTERACTIVE AND AUTOMATED TISSUE IMAGE ANALYSIS WITH GLOBAL TRAINING DATABASE AND VARIABLE-ABSTRACTION PROCESSING IN CYTOLOGICAL SPECIMEN CLASSIFICATION AND LASER CAPTURE MICRODISSECTION APPLICATIONS", filed on Sep. 13, 2002 which is incorporated herein by reference in its entirety.

FIELD OF THE INVENTION

The invention relates generally to automated tissue image analysis, and in particular, to image analysis for cell classification and laser capture microdissection applications.

BACKGROUND OF THE INVENTION

Laser capture microdissection (LCM) is a robust and reliable technology for isolating pure populations of cells from heterogeneous tissue samples for subsequent analysis. The LCM technology integrates a laboratory microscope with a low-energy laser and transfer film in a convenient one-step, aim-and-shoot method. Generally, thin sections of tissue samples are mounted on standard glass slides employing various common methods known in the art such as fixing tissues with alcohol-based precipitation techniques. LCM is compatible with various common methods for the preparation of tissue sections.

The thin tissue sections may be stained by standard techniques such as hematoxylin and eosin, methylene green nuclear stain, fluorescence in situ hybridization, or immunohistochemistry for identification of tissue morphology and cell populations of interest. Staining the sample may or may not be required. In some cases, a marker is added to the tissue sample to adhere to a specific type of site in the tissue to render the site detectable in an image of the tissue that is captured via an acquisition system. Markers may be antibodies, drugs, or other compounds that attach or bind to the tissue component of interest and are radioactive or fluorescent or have a distinctive color or otherwise detectable. Once mounted on a substrate surface such as a standard glass slide, the transfer film is located in juxtaposition to the tissue surface. The transfer film is typically made of thermoplastic film such as ethylene-vinyl acetate. Broadband energy absorbing transfer films are described in U.S. Pat. No. 6,495,195 entitled "Broadband absorbing film for laser capture microdissection" issued to Baer et al. and hereby incorporated by reference in its entirety.

Once loaded in a LCM device, a tissue sample is viewed via a microscope and a cell or cells of interest are targeted. The laser is directed at the cell or cells of interest and pulsed to provide enough energy to transiently and locally melt the thermoplastic film and activate the transfer film in the precise focal region of the laser beam. The laser beam spot size can be adjusted so that a targeted individual cell or cluster of cells can be selected in one or more pulses of the laser. The optical system of a LCM instrument is described in U.S. Pat. No. 6,215,550 and U.S. Pat. No. 6,512,576 both entitled "Laser capture microdissection optical system" and issued to Baer et al. and both hereby incorporated by reference in its entirety.

The cell or cells in the activated region of the transfer film adhere to the transfer film and can be extracted from the remaining tissue sample with the unselected tissue remaining in contact with the glass slide. Because the thermoplastic film absorbs most of the thermal energy and the pulse lasts for a fraction of a second, no detectable damage of the biological macromolecules occurs. Once removed from the tissue sample, the selected cell or cells are subjected to appropriate extraction conditions for ensuing molecular analysis. To facility subsequent extraction steps, the transfer film can be mounted on a substrate surface that is shaped like a cap that fits a microcentrifuge tube as described in U.S. Pat. No. 6,157,446 entitled "Laser capture microdissection analysis vessel" issued to Baer et al. and hereby incorporated by reference in its entirety and in U.S. Pat. No. 5,859,699 entitled "Laser capture microdissection analysis vessel" issued to Baer et al. and hereby incorporated by reference in its entirety. A method for manufacturing a consumable is described in U.S. Pat. No. 5,985,085 entitled "Method of manufacturing consumable for laser capture microdissection" issued to Baer et al. and hereby incorporated by reference in its entirety. Laser capture microdissection is also described in U.S. Pat. No. 6,469,779 entitled "Laser capture microdissection method and apparatus" issued to Baer et al. and hereby incorporated by reference in its entirety.

By isolated only target cells from the tissue sample using LCM, researchers can immediately analyze the gene and enzyme activity of the target cells using other research tools. Such procedures as polymerase chain reaction amplification of DNA and RNA, and enzyme recovery from the tissue sample have been demonstrated. No limitations have been reported in the ability to amplify DNA or RNA from tumor cells extracted with laser capture microdissection. LCM has been particularly advantageous in identifying the differences between expression levels in normal and diseased tissues. In addition to combining LCM with several genomic and proteomic techniques to document the progression of normal cells to premalignant and metastatic cancer cells in various tissues, microdissected cells are also used in applications for gaining new insights in developmental biology.

The LCM technique has been automated as described in International Patent Publication No. WO 01/33190 entitled "Automated laser capture microdissection" to Baer et al. and hereby incorporated by reference in its entirety and in International Patent Publication No. WO 02/037159 entitled "Road map image for automated microdissection" to Baer et al. and hereby incorporated by reference in its entirety. Continued automation of the LCM process is desired. In particular, automated tissue image analysis for target cell classification for subsequent laser capture microdissection is wanting for high-throughput batch processing. This invention addresses these needs for increased automation, accurate and reliable image analysis and cell classification for LCM.

Tissue analysis and identification of a cell or a region of interest (ROI) have always been a time-consuming, laborious process. The major obstacles to the successful deployment of a high-throughput tissue analysis system are the diversity in the ROIs and cell types, the variability in staining, and the skepticism from the user community.

There exists an abundance of literature and prior art in the field of automated tissue recognition. U.S. Pat. No. 6,327,377 issued to Rutenberg, et al. entitled "Automated cytological specimen classification system and method" uses a primary detector based on thresholding of an integrated optical density (IOD), a secondary classifier that utilizes a three-layer back-propagation neural network for pattern matching, and a tertiary screener by a human operator. Another U.S. Pat. No. 6,215,892 issued to Douglas et al. entitled "Method and apparatus for automated image analysis of biological specimens" uses a color-ratio threshold as an initial detector followed by a morphology-based analysis for identifying potential ROI candidates. U.S. Pat. No. 5,987,158 issued to Meyer et al. entitled "Apparatus for automated identification of thick cell groupings on a biological specimen" takes a slightly different approach to ROI classification. After image segmentation, it uses Fisher's linear binary decision tree in series to perform object (ROI) classification.

Unfortunately, none of these patents address the core issue of how to facilitate high-throughput cell classification processing that yields robust performance through the creation and manipulation of global training databases to ease the burden on human operators. Furthermore, modern nonparametric learning algorithms for studying gene activation patterns and regulatory networks require a lot of high-quality data. This invention bridges the gap by providing a flexible, high-throughput cell classification processing chain in two complementary dimensions to improve system performance with age.

BRIEF SUMMARY OF THE INVENTION

In accordance With one aspect of the invention, there is provided a computer method for image analysis. The method includes the step of receiving an image. The image is transformed into a feature space. At least one region of interest (ROI) at a pixel level of processing is selected and features from the ROI at a pixel level of processing are extracted. Also, at least one non-ROI at a pixel level of processing is selected and features from the non-ROI at a pixel level of processing are extracted. The extracted features are ranked based on feature performance for successful detection of a selected ROI at a pixel level of processing and the ranked extracted features are recorded. A classification algorithm is selected and executed to classify the image into regions of interest at a pixel level of processing. The resulting ROIs based on pixel processing are recorded for further processing.

In accordance with another aspect of the invention, there is provided a computer method for image analysis. The method includes the step of receiving a first image. The first image is transformed into a feature space and a level of abstraction is selected. A database containing parameters based on the selected level of abstraction is also selected. The first image is classified into regions of interest employing the parameters from the database based on the selected level of abstraction. The parameters of the database for the level of abstraction are updated with data from the first image. The method further includes the step of receiving a second image and transforming the second image into a feature space. The second image is classified into regions of interest employing the updated parameters from the database based on the selected level of abstraction. The parameters of the database are updated with data from the second image.

BRIEF DESCRIPTION OF THE SEVERAL VIEWS OF THE DRAWINGS

The foregoing and other advantages of the invention will become apparent upon reading the following detailed description and upon reference to the drawings in which.

Figure 1:
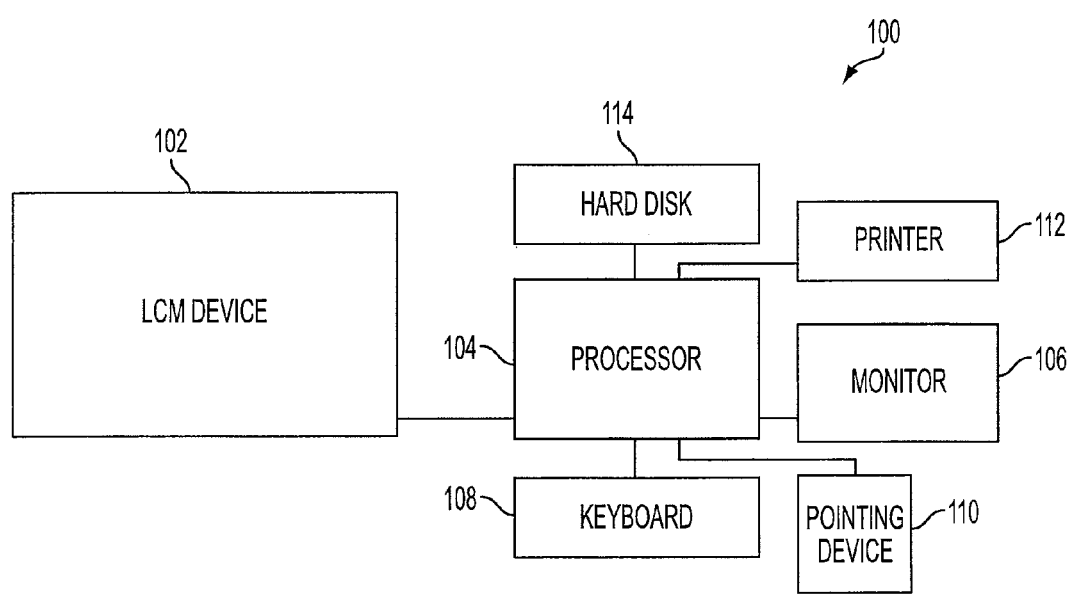
FIG. 1 is a schematic diagram of the apparatus of the invention.

While the present invention is susceptible to various modifications and alternate forms, specific variations have been shown by way of example in the drawings and will be described herein. However, it should be understood that the invention is not limited to the particular forms disclosed. Rather, the invention is to cover all modifications, equivalents, and alternatives falling within the spirit and scope of the invention as defined by the appended claims.

DETAILED DESCRIPTION OF THE INVENTION

This application claims priority to U.S. Provisional Application Ser. No. 60/410,433, entitled "INTERACTIVE AND AUTOMATED TISSUE IMAGE ANALYSIS WITH GLOBAL TRAINING DATABASE AND VARIABLE-ABSTRACTION PROCESSING IN CYTOLOGICAL SPECIMEN CLASSIFICATION AND LASER CAPTURE MICRODISSECTION APPLICATIONS", filed on Sep. 13, 2002 which is incorporated herein by reference in its entirety. This application also claims priority to U.S. application Ser. No. 09/707,313 entitled "AUTOMATED LASER CAPTURE MICRODISSECTION", filed on Nov. 6, 2000, which is incorporated herein by reference in its entirety.

A schematic diagram of the apparatus 100 of the invention is shown in FIG. 1. The apparatus 100 of the invention comprises a laser capture microdissection (LCM) device 102 coupled to a central processor 104. The processor 104 is connected to a variety of input and output devices including a monitor 106, keyboard 108, a pointing device 110 such as a mouse, and a printer 112. A hard disk 114 is connected and controlled by the processor 104. The processor 104 is an IBM PC/AT or compatible although it may be another computer-type device suitable for efficient execution of the functions described herein. The processor 104 controls the functioning and flow of data between components of the LCM device 102, causes execution of a variety of classification and other algorithms and handles storage of image and classification information. The invention may be embodied in software, on a computer readable medium or on a network signal, to be run on a general purpose computer or on a network of general purpose computers. As is known in the art, the neural network component may be implemented with dedicated circuits rather than with one or more general purpose computers.

Figure 2:
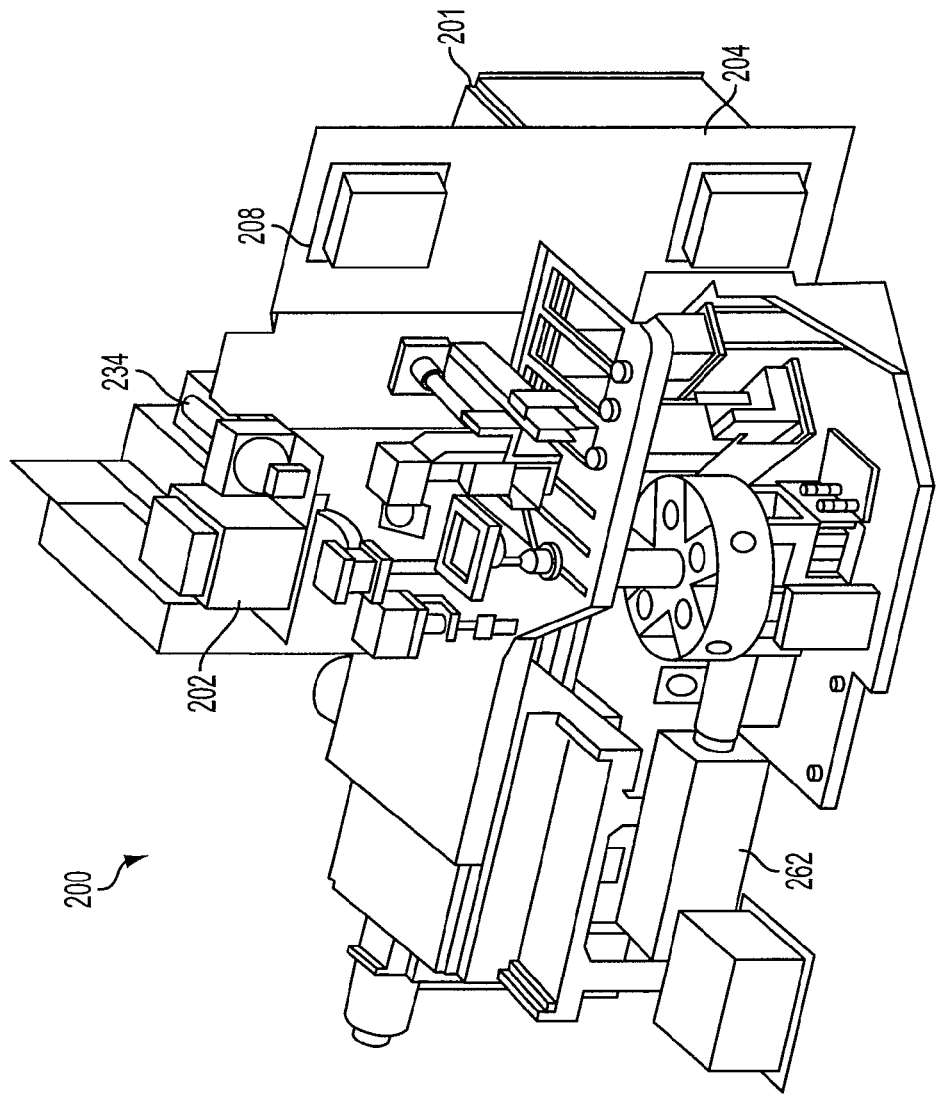
FIG. 2 is a perspective view of a portion of the automated LCM device.
Figure 3:
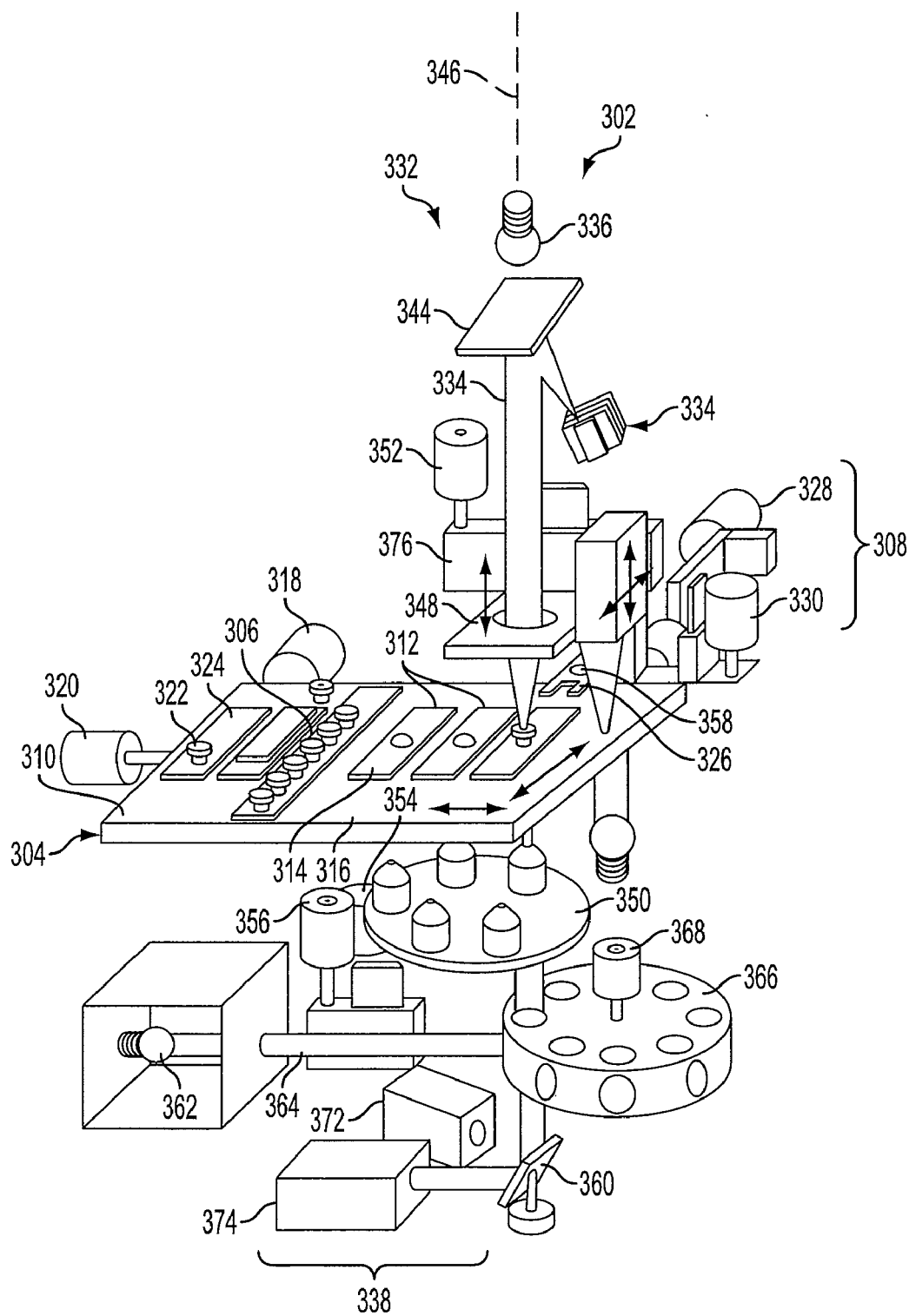
FIG. 3 is a exploded top level block diagram of a portion of the automated LCM device.

With reference now to FIGS. 2 and 3, the LCM device 102, which is connected to and controlled by the processor 104, will now be discussed. The LCM device 200 comprises an illumination and laser optical subsystem 202, 302 interconnected with a translation stage 204, 304, a transfer film carrier supply 306, and a transfer film carrier handling subsystem 206, 308.

The translation stage 204, 304 includes a work surface 310 adapted to receive at least one sample carrier 312. The sample carriers 312 are depicted in FIG. 3 as standard microscope slides having samples 314 attached thereto. The translation stage 304 defines at least one beam path hole (not shown) corresponding to an at least one sample carrier receiving location 316 such that light may pass through the sample 314, sample carrier 312 and translation stage 304. A vacuum chuck, having one or manifold holes and conduits at the carrier receiving location 316, is employed to secure the sample carrier 312 in position when the vacuum is engaged. The translation stage 304 is automated by a fore-and-aft motor 318 and a translation stage side-to-side motor 320 both of which are controlled by the central processor 104.

The transfer film carrier supply 306 is located adjacent to the translation stage 304. The transfer film carrier supply 306 is connected to the translation stage 304 or located on a nearby element separate from the translation stage 304. The transfer film carrier supply 306 is adapted to receive and serve as a staging area for transfer film carriers 322. In FIG. 3, the transfer film carriers 322 are depicted in the form of discrete consumables and shaped in the form of caps that are adapted to mate with reaction vessels for post-capture processing. The caps include a laser capture microdissection transfer film (not shown) attached to the lower surface of the cap.

The transfer film carrier handling subsystem 208, 308 is an automated assembly for picking transfer film carriers 322 from the transfer film carrier supply 306 and placing them in juxtaposition to the tissue samples 314 located on sample carriers 312 prior to cell capture. After cell capture, the transfer film carrier handling subsystem 208, 308 removes the transfer film carriers 322 and delivers them to an output station 324 that is also located adjacent to the translation stage 204, 308. The output station 324 is a standard microscope slide onto which the transfer film carriers 322 are placed. Alternatively, the output station 324 is a capping station for automatically mating the caps with reaction vessels such as microcentrifuge tubes for post-LCM processing.

The transfer film carrier handling subsystem 208, 308 is automated and controlled by the processor 104. The transfer film carrier handling subsystem 208, 308 includes an arm 326 having a working end adapted to pick and place a transfer film carrier 322. The arm 326 is controlled by a carrier translation motor 328 and a carrier lift motor 330 included in the subsystem 308. The arm 326 includes at least a load position and at least an inspect position. While in the load position, the working end of the arm 326 is located adjacent to the transfer film carrier supply 306. In this position, the arm 326 is manipulated by the motors 328 and 330 to pick up a transfer film carrier 322 from the transfer film carrier supply 306. From the load position, the arm 326 is manipulated automatically to the inspect position. While in the inspect position, the working end of the arm 326 is located adjacent to the sample carrier 312 and the arm 326 is manipulated to place the transfer film carrier 322 into precise juxtaposition with the sample 314. After LCM is complete, the arm 326 removes the transfer film carrier 322 and is automatically manipulated to an unload position. In the unload position, the working end of the arm 326 is located adjacent to the output station 324 where it is manipulated to release the transfer film carrier 322 and/or to mate the transfer film carrier 322 with a reaction vessel. The sample carrier handling subsystem 308 is described in greater detail in U.S. patent application Ser. No. 09/707,313 filed on Nov. 6, 2000, entitled "Automated Laser Capture Microdissection," the contents of which is hereby incorporated by reference in its entirety.

The illumination and laser optical subsystem 202, 302, which is connected to and controlled by the processor 104, comprises an optical system 332 interconnected to a laser 334, an illuminator 336 and an image acquisition system 338. The illumination and laser optical subsystem 302 is a modified inverted microscope and laser system. The laser 334, for example, has laser diodes made of gallium arsenide with aluminum doping (AlGaAs) and emits radiation at approximately 800 nm. The laser 334 is controlled by the processor 104 and is selectively activable to emit a laser beam 340.

The illumination and laser optical subsystem 302 also includes an illuminator 336. The illuminator 336 is controlled by the processor 104 and is selectively activable to emit light 342 to illuminate the sample. In typical microscopes, the illuminator 336 is, for example, a condenser or tungsten-halogen lamp. According to one aspect of the invention, the illuminator 336 is a light emitting diode (LED). The illuminator 60 is particularly important because of the need for consistency in the light source used to illuminate samples especially when performing automated cell recognition based on image processing using sophisticated software employing color-based algorithms. Typically, the light source for a microscope system is a halogen lamp. These lamps are low cost and provide illumination at a color temperature of approximately 3200 K when operating at their designed voltage and power levels such as 6 volts and 30 watts. A limitation of these lamps is that as the voltage and power levels are decreased, the color temperature of their output shifts towards the red-end of the spectrum. This shift in color causes the image of the sample illuminated in the instrument to shift in color. The human eye can deal with this color shift to some extent but an imaging system employing a camera and image processing software cannot adapt so easily. Because the camera is highly light-sensitive, the user will often reduce the illuminator power in order to prevent saturation of the camera by the illuminator. This reduction in power shifts the illuminator color temperature. The camera system will display the colors based on its baseline calibration, and if the illumination source is red-shifted, then the camera image will also be red-shifted. The shift in color can cause serious problems with image recognition systems, particularly those employing learning files that are applied across multiple images as will be discussed in detail hereinbelow. For example, if the image recognition system learning file was trained at one color temperature, then its ability to recognize subsequent images taken at another color temperature resulting from slightly different lamp power settings, can be seriously impaired. In one variation of this invention, a white LED is employed as the illuminator 336 because the spectral characteristics of the LED do not change significantly with applied current. The variation in color temperature with lamp intensity is eliminated allowing the laser microdissection process including image recognition to be enhanced. In another variation, multiple LEDs of different colors, such as red, green and blue, are employed and mixed together and used to continuously adjust the color of the system by varying the amount of each color in the mix. In yet another example, rotating crossed polarizers or variable neutral density filters are located between the illuminator 336 and a partially-transmissive and partially reflective surface 344 to adjust the light intensity at a sample 314 while leaving the illumination lamp 336 at its maximum setting.

The optical system 332 of the illumination and laser optical subsystem 302 has an optical axis 346 as shown by the dashed line in FIG. 3. The optical system 332 comprises at least a partially transmissive and a partially reflective surface 344, a focusing lens 348, and an objective 350. The partially transmissive and partially reflective surface 344 is optically coupled to a focusing lens 348 that is in turn optically coupled to an objective 350. The optical system 332, in turn is optically connected to the laser 334, illuminator 336, and acquisition system 338.

The optical system 332, laser 334 (shown with reference numeral 234 in FIG. 2), illuminator 336 and acquisition system 338 are configured such that the laser light beam 340 passes from the laser 334 to the partially transmissive and partially reflective surface 344. The partially transmissive and partially reflective surface 344 is, for example, a dichroic mirror. From the partially transmissive and partially reflective surface 344, the laser beam 340 passes through the focusing lens 348.

The focusing lens 348 is connected to a laser focus motor 352 which is controlled by the processor 104 and operates to control the focusing lens 348 to focus and adjust the laser beam spot size from a smaller tightly focused condition to a relatively larger beam spot size arising from a relatively defocused laser beam. In one variation, the focusing lens 348 is replaced with a stepped lens. In another variation, a variable aperture is optically coupled to the focusing lens 348 to adjust the laser beam spot size.

From the focusing lens 348, the laser beam 340 is directed along the optical axis 346 toward the translation stage 304. In particular, the laser is precisely directed at targeted cells of a tissue sample on a sample carrier 314 positioned in a sample carrier receiving location 316. The laser beam 340 passes through the beam path hole in the translation stage to a cut-off filter that reflects or absorbs energy from the laser beam.

Light 342 from the illuminator 336 passes to the partially transmissive and partially reflective surface 344 and then through the focusing lens 348 along the optical axis 346 and through the beam path hole of the translation stage 304. From the translation stage 304, illumination light 342 passes through the objective 350 and then to the acquisition system 338. Light 342 from the illuminator 336 and the laser light beam light 340 are superimposed at the partially transmissive and partially reflective surface 344 along the optical axis 346. The objective 350 comprises an objective changer with a series of microscope objectives deployed on an objective turret wheel. The objective 350 is automated by an objective changer motor 354 and controlled by the processor 104 to select an appropriate objective lens. The objective 350 is also automated by an objective focus motor 356 to focus illumination light 342 passing through the beam path hole of the translation stage 304.

In one variation, the optical system 332 further includes a collimator lens and condenser lens (not shown) such that the partially transmissive and partially reflective surface 344 is located between the collimator lens and the condenser lens. Also, a scattering media is included and located between the condenser lens and the translation stage 304 and above the sample 314. As shown in FIG. 3, the scattering media is a piece of diffuser glass 358, for example, located integrally with the working arm 326 of the transfer film carrier handling subsystem 308 and adapted to be positioned in and out from within the optical axis 346. Illumination light 342 is diffused by the scattering media illuminating the sample from all angles. This high illumination angle or high numerical aperture illumination provides high image quality and eliminates the need for refractive index matching of a sample. Such a scattering media allows visualization of the cell nucleus and other sub cellular structures that would normally be obscured by normal illumination techniques. The scattering media is, for example, a diffuser material such as milk or opal glass, frosted glass, standard printer/photocopier paper, a lenticular sheet, a volume diffuser or a surface diffuser. In one variation, the scattering media is integral with the transfer film carrier 322 or transfer film itself. Illumination light and laser beam light steering mirrors 360 are employed where necessary to direct light.

In one variation, the illumination and laser optical subsystem 302 includes a fluorescent light source 362 coupled to the optical system 332 and controlled by the processor 104. The light source 362 is, for example, an EPI-fluorescent xenon or mercury lamp that emits light 364 having a specific wavelength or within a specific wavelength range. The specific wavelength or wavelength range of a beam emitted by the light source 362 is selected by a fluorescence filter wheel 366 operated by a fluorescence filter changer motor 368 to excite a fluorescent system (e.g., chemical markers and optical filtering techniques that are known in the industry) that is incorporated in or applied to the sample 314. The sample 314 includes at least one member selected from the group consisting of chromophores and fluorescent dyes, synthetic or organic and the frequency of the beam emitted by the fluorescence laser 362 (shown as element 262 in FIG. 2) is tuned to match the at least one member. The fluorescent laser beam 364 is superimposed with the laser beam 340 and light 342 from the illuminator 336. Fluorescence emitted by the sample is optionally amplified by the objective 350, reflected by a camera changer mirror 360 and captured for viewing by the acquisition system 338. The objective changer motor 354 and the objective focus motor 356 operate to adjust the fluorescent laser beam 364 and the emitted fluorescent beam.

The acquisition system 338 includes one or more CCD cameras positioned in the optical path to capture a focused, magnified electronic image of an area of the sample. As shown in FIG. 3, the acquisition system 338 includes a black-and-white camera 372, a color camera 374 and a roadmap camera 376 for capturing appropriate images. The acquisition system 338 is coupled to and controlled by the processor 104 delivering images thereto for image processing, viewing and navigation purposes. The color camera 374 may be a conventional RGB camera, or other camera able to provide suitable information of the specimen or image to the computer. The roadmap camera 376 and its navigational functions and features are explained in detail in U.S. patent application Ser. No. 09/707,313 filed on Nov. 6, 2000, entitled "Automated Laser Capture Microdissection" and incorporated herein by reference in its entirety. The LCM device includes an electronics panel (marked with reference numeral 201 in FIG. 2) comprising printed circuit boards and instructions for the automated LCM device 102, computer interface cards and input/output devices for connecting and communicating with the central processor 104.

The apparatus 100 operates to carry out the following general steps for laser capture microdissection. First, a tissue or sample smear 314 is fixed onto a standard microscope slide or sample carrier 316 by routine protocols. Typically, the sample is fluorescently stained. Histochemical staining is especially useful for identification of cells of interest. Immunological labeling is another method that is used to identify a cell of interest. According to this technique, an antibody specific for an antigen whose presence or absence is characteristic of a rare cell of interest is bound to the cell and directly or indirectly labeled with a fluorescent stain. Immunolabeling and staining techniques are well known in the art and incorporated herein by reference.

Next, the sample carrier 314 is introduced into the LCM device 102 at a sample carrier receiving location 316. A transfer film is placed in juxtaposition to the sample, either in contact with the sample or separated from the sample by a small distance. Typically, the transfer film is attached to a substrate surface of the transfer film carrier or cap. The transfer film is, for example, an approximately 100-micron thick ethyl vinyl acetate (EVA) film available from the Electroseal Corporation of Pompton Lakes, N.J. The transfer film is manufactured containing organic dyes that are chosen to selectively absorb in the near infrared region of the spectrum overlapping the emission region of laser that is employed, typically an AlGaAs laser. Basically, the transfer film is selected and/or dyed or filled with energy-absorbing matter to absorb energy at the wavelength emitted by the laser.

The illuminator 336 illuminates the sample. Simultaneously, the EPI-fluorescent lamp 362 is turned on to activate the fluorescent markers in the sample 314. Also, the laser beam is activated in idle mode such that the laser beam light provides a visible low amplitude signal that can be detected during live viewing via the acquisition system for visual alignment and targeting or when adjustment of the beam spot size is desired. As previously mentioned, the laser beam spot size is adjusted by operating the laser focus motor 352 to move the focusing lens 348. An image is capture via the acquisition system 338 and delivered to the processor 104 for target cell detection. Target cell detection is performed manually or automatically. Novel automated and semi-automated target cell detection methods will be discussed in detail hereinbelow. After target cells are detected and located, the processor automatically directs the laser beam path such that it is coincident with the location of target cells and simultaneously activates the laser into pulse mode. In pulse mode, the laser beam light activates the transfer film such that the activated portion of the transfer film increases in temperature, expands and adheres to the tissue region of targeted cells. Once the desired target cell or cells are adhered to the transfer film, the transfer film is lifted from the sample and the selected portion of tissue comprising targeted cells is removed with the film. The targeted cells are then ready for post-LCM processing.

Figure 4:
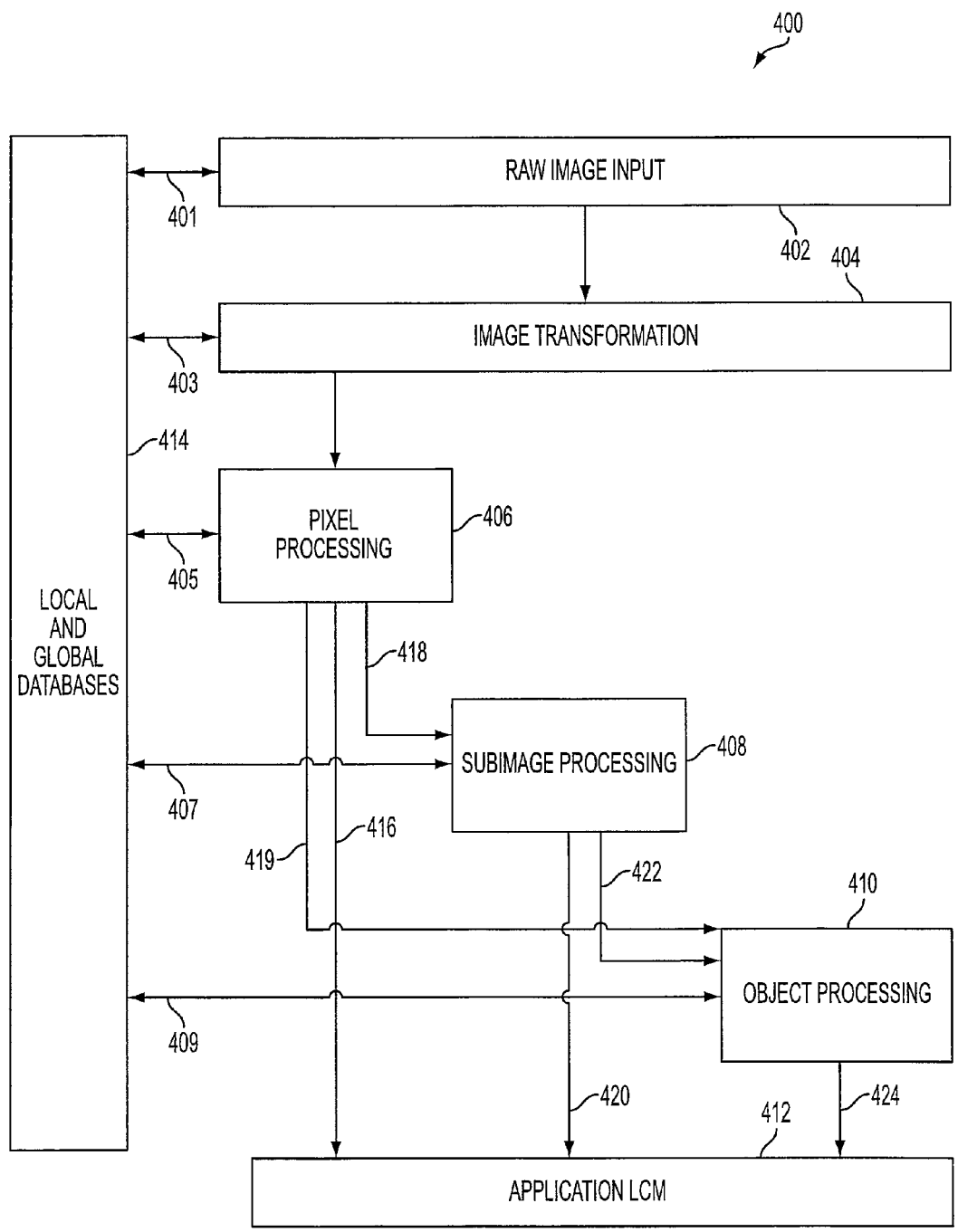
FIG. 4 is a block diagram representation of a method of classifying objects according to the invention.

Automated and semi-automated target cell recognition methods will now be discussed. FIG. 4 is a block diagram representation 400 of a method of classifying objects according to the invention in which focused and magnified electronic images captured by one or more cameras of the acquisition system are transmitted to the processor for image processing and classification of the cells appearing in the imaged area. The raw image, preferably represented by electrical signals, is delivered to the computer processor 402. The raw image data is stored in and retrieved from various databases 414 as shown by line 401. The raw image data undergoes image transformation 404 and is stored in one or more databases as shown by line 403 before commencing classification under one or more than one of the classification protocols: pixel processing 406, subimage processing 408, and object processing 410. One or more classification protocols are executed for image processing and classification of the cells appearing in the imaged area prior to commencing the steps of a desired application 412 such as extracting classified cells using laser capture microdissection. Throughout the method of operation, various databases 414 are generated and employed interactively along each processing stage, pixel 406, subimage 408 and object 410 along lines 405, 407 and 409, respectively.

The invention performs region-of-interest (ROI) identification in two processing dimensions. The first processing dimension utilizes variable abstraction processing. Pixel processing 406 is a first level of abstraction that relies on a number of attributes, such as red (R), green (G), blue (B), hue (H), saturation (S), intensity or value (V), gray intensity after RGB-to-gray conversion and histogram equalization (GI), red/green (RG), red/blue (RB), green/blue (GB), to perform classification. Instead of using a single attribute, pixel processing uses an appropriate composition of pixel attributes that are optimized automatically for each database. Subimage processing 408 is a second level of abstraction that utilizes attributes, such as texture-related information and neighborhood statistics at an arbitrary subimage level that is selected by the user that is tailored to the tissue types in study, to exploit the level of information available at the variable-size image level. Object processing is a third level of abstraction that extracts features at the object level such as morphology, gradient, and texture information at the object level to perform ROI identification.

As shown by the arrows in FIG. 4, the transition from pixel processing 406 to subimage processing 408 to object processing 410 is not a rigid transition. Instead, the invention employs a flexible state transition so that processing steps are tailored to the complexity of the image being analyzed. For example, pixel processing 406 may be more than adequate for the classification of a particular image dataset thereby eliminating the need for subimage 408 or object processing 410. In such a case, processing proceeds directly from pixel processing 406 to LCM 412 as shown by arrow 416. If the classification performance results are inadequate for a particular image data set, the processing may proceed from pixel processing 406 to subimage processing 408 along line 418 and then from subimage processing 408 to LCM along line 420. Alternatively, image recognition processing may proceed from pixel processing 406 to object processing 410 via arrow 419 and then from object processing 410 to LCM 412 via line 424. Alternatively, processing steps may proceed through all three levels of abstraction before LCM 412 following arrows 418, 422 and 424.

A focused and magnified electronic image from the microscope and captured by a camera of the acquisition system 338 is transmitted to and digitized into a pixel data image by the processor at block 402 and is stored in a database 414. The raw image data in a .jpg or .tff file format, then undergoes image transformation 404 in which a number of image processing and evaluation functions are performed and the raw image data is converted into an RGB digital space, an HSV space, and a color ratio space employing image processing techniques well known in the art. The RGB-to-HSV transformation, for example, is found at Internet address disney.ctr.columbia.edu/jrsthesis/node29 and incorporated herein by reference in its entirety. For a raw image comprising L×M pixels, a two-dimensional feature space, L×M matrix of one-by-ten feature vectors comprises the transformation output. Each one-by-ten feature vector for each pixel location includes an associated feature value for each pixel location, (l, m), for example, in the form of 10×1 vectors in the [R, G, B, H, S, V, GI, RG, RB, GB]. The transformation output data space and the associated raw image data are saved to a hard disk as a data file and marked with appropriate identifiers. The next step is pixel processing 406.

Figure 5:
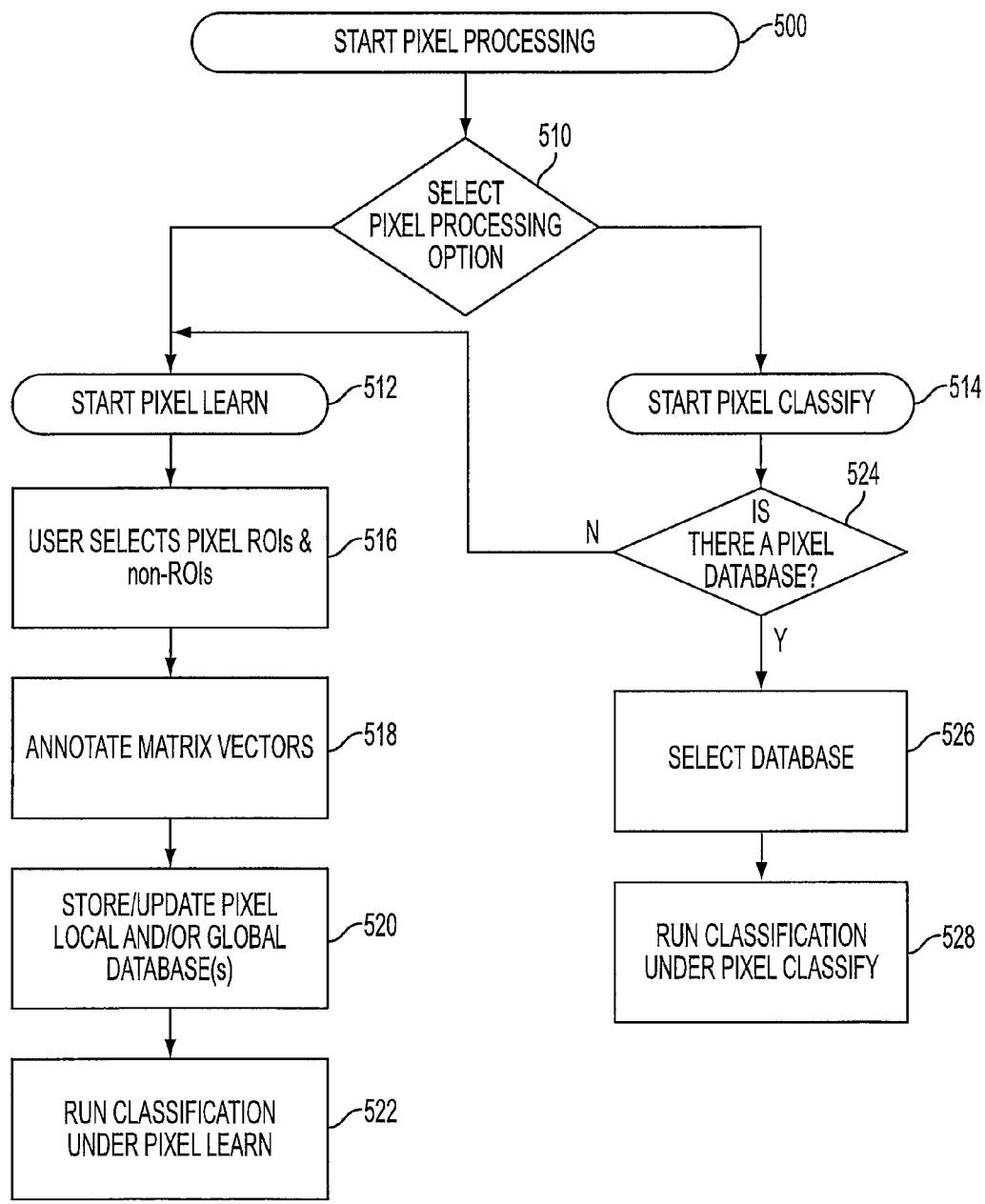
FIG. 5 is a block diagram representation of a method of pixel processing according to the invention.

Referring now to FIG. 5, at the start of pixel processing 500, a user retrieves a data file and views a current image that is most convenient for manual user observation, for example, the user views either the raw image, the RGB digital space, HSV space or color ratio space on the computer monitor. Before proceeding with the classification, the user selects one of two pixel processing protocol options at step 510 from the graphical user interface prompt. One of the protocol options is called "PIXEL LEARN" 512 and the other is called "PIXEL CLASSIFY" 514. The user chooses "PIXEL CLASSIFY" 514 if an existing database that has already been trained is to be employed and applied to the current image for automated classification. The "PIXEL CLASSIFY" option will be discussed in detail hereinbelow. The "PIXEL LEARN" 512 option is chosen if the user does not wish to employ an existing database, an existing database is not suitable for the tissue sample and image at hand or a database has not been trained such that it can be applied to the current image. "PIXEL LEARN" 512 enables the user to create a new database for the current image. The database that is created under "PIXEL LEARN" 512 for the current image is stored and may also be concatenated to a variety of other new or existing, local or global type databases. Database information management will be discussed in detail hereinbelow.

"PIXEL LEARN" is processing along the learning and automatic classification axis or second dimension processing as opposed to the variable abstraction axis discussed above. "PIXEL LEARN" and the second dimension of learning and automatic classification permits the system to become more intelligent with time as data and processing results from one or more "PIXEL LEARN" operations are stored in various databases as will be described hereinbelow. In general, the learning stage requires interactive processing with end user participation in which the end user participates by providing a number, preferably at least three, of ROI and non-ROI selections for a small number of images. It should be noted that the number of images is less relevant than the number of ROI and non-ROI selections in terms of pixels, subimages, and objects. The reason is that if an image can provide a lot of relevant example pixels and it is representative of the true operating space, then only one image may be sufficient. If a particular image has very little relevant tissues, then more images may be required to create a learned database. Then, the system takes over and creates individual trained databases, which are then concatenated to form local or global databases for use with the "PIXEL CLASSIFY" option 514, which is automated and requires little end user participation. The "PIXEL LEARN" 512 option will now be discussed in greater detail.

In "PIXEL LEARN" 512 under the pixel processing protocol 500, the user selects at least one region of interest (ROI) 516 from the image viewed on the computer monitor using a mouse or some other pointing device coupled to the computer. A ROI is a desired target location to be captured via laser capture microdissection and may include an abnormal cell or cells, malignant or premalignant cell or cells or otherwise a cell or cells of interest. Preferably, the user selects three or more ROIs. Next, the user is prompted to select at least one non-ROI 516, or region that is not of interest for the application. Examples of non-ROIs include healthy cells or other background matter or clutter. Of course, the ROIs are not limited to the examples shown herein, such that a ROI may, of course, be a healthy cell selection. Nonetheless, the type of ROI selected should be consistent for each database. Preferably, the user also selects three or more non-ROIs. Each selection or exemplar made by the user segments the image and annotates the transformation output vector of the pixel location or locations of the selection or selections with another value that identifies the type of selection, ROI or non-ROI, for the pixel location or locations that were manually selected by the user 518. The annotation to the vector is a binary value such that, for example, the number "1" is used for non-ROI selections and the number "2" is used for ROI selections. Therefore, vectors in a two-dimensional, L×M matrix associated with ROI or non-ROI selections are augmented to one-by-eleven vectors wherein, for example, a ROI-selected pixel is denoted by a vector in the form [R, G, B, H, S, V, GI, RG, RB, GB, 2] and a non-ROI-selected pixel is denoted by a vector in the form [R, G, B, H, S, V, GI, RG, RB, GB, 1]. The matrix is stored in the data file associated with the image 520.

Alternatively, an N×3 array is created wherein N is the number of ROI and non-ROI manual selections made by the user. The array includes the pixel location (x, y) and the corresponding class indices such as 1 for non-ROI and 2 for non-ROI. Hence, a vector in the array will be of the form [x, y, 2] for a ROI and [x, y, 1] for a non-ROI segment. In addition to the image file, this array is another input under the "PIXEL LEARN" processing option.

Also, the L×M matrix or, alternatively, the N×3 matrix together with the image file is stored in a local pixel database 520. A local database is created and classified in any number of ways. For example, a local database can consist of data associated with a particular image or a particular type of tissue or stain used. Another example of a local pixel database is a patient-specific database. In general, a variety of local pixel databases may be created and/or updated.

The information can also be stored in a global database. A global database, for example, can be all the information associated with pixel processing selections regardless of tissue type and stain. Each time "PIXEL LEARN" is chosen appropriate databases are automatically or manually concatenated to improve system performance with time. For example, all data associated with one tissue sample collected over more than one image can be concatenated into one database. Another example is the concatenation of all data associated with a particular tissue type. In general, a variety of global databases can be created and/or updated.

Figure 6:
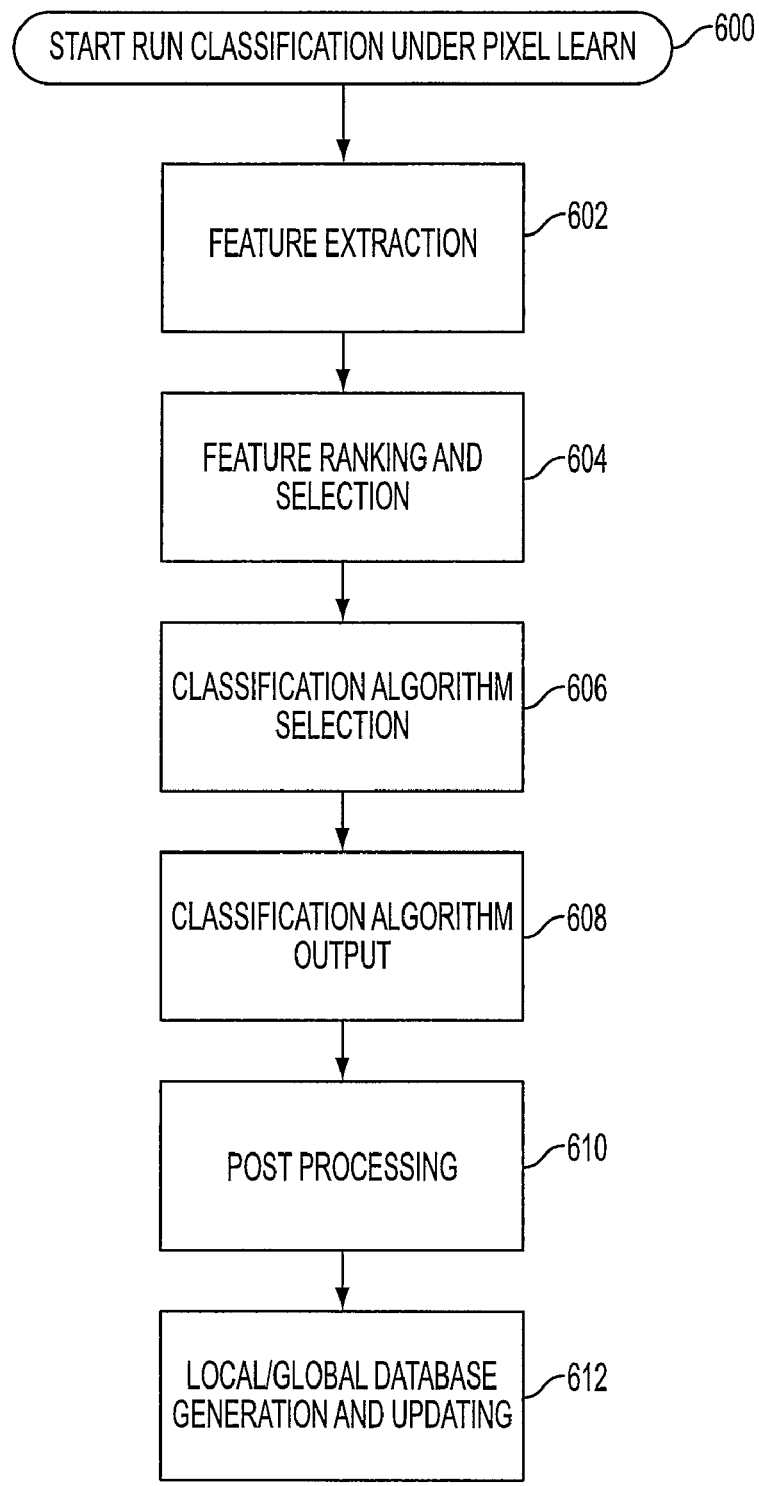
FIG. 6 is a block diagram representation of a method of run-classification under the "PIXEL LEARN" processing option according to the invention.

The next step is classification 522 under "PIXEL LEARN." Referring now to FIG. 6, there is depicted the steps comprising classification. At the start of classification 600, the first step is feature extraction 602. In feature extraction, features are measured and calculated and a matrix of 11×1 vectors of feature values and ROI/non-ROI annotations, such as red (R), green (G), blue (B), hue (H), saturation (S), intensity or value (V), gray intensity after RGB-to-gray conversion and histogram equalization (GI), red/green (RG), red/blue (RB), green/blue (GB), non-ROI (1), ROI (2) represented by the exemplary vector [R, G, B, H, S, V, GI, RG, RB, GB, 1], is compiled from each ROI and non-ROI selection made by the user for a particular data set at the pixel level.

The next step is feature ranking 604 in which the pixel features [R, G, B, H, S, V, GI, RG, RB, GB] are ranked according to their effectiveness in discriminating ROIs. Feature ranking is performed using any combinatorial optimization algorithm known in the art such as add-on or forward-backward ranking algorithm to first iteratively rank each single feature (singlet), R, G, B, H, S, V, GI, RG, RB, GB, from best feature to worst feature. Feature performance is based on the degree of successful detection of a ROI annotation that is made by the user and reserved for performance testing. For example, if a user selects four ROIs, two ROI selections will be reserved to test the performance of features obtained from the other two ROI selections. Each singlet will be then ranked accordingly using the combinatorial optimization algorithm.

The combinatorial optimization algorithm proceeds to then iteratively rank pairs of features (doublets). For example, the first ranked singlet will be paired with another feature and the performance of both features in combination will be ranked against other doublets. The combinatorial optimization algorithm proceeds to then iteratively rank sets of three features (triplets). For example, the first ranked doublet will be combined with another feature to form a triplet of features, which will be ranked against other triplets. The algorithm ranks singlets, doublets, triplets, and quadruplets and so on until the improvement in performance for detecting a ROI reaches a predetermined value or point of diminishing returns at which point a feature singlet, doublet or triplet is selected. For example, the highest ranked triplet may provide only a small percent increase in performance over the highest ranked doublet in which case, the doublet would be the selected feature combination to be employed in classification under "PIXEL LEARN." This estimation of the point of diminishing returns advantageously enhances real-world performance by avoiding data-overfitting or memorization during learning. That is, the iterative optimization algorithm automatically finds the minimum feature dimension that offers the best classification accuracy. The result of the optimization algorithm is an optimal feature subset (x), e.g., a singlet, doublet, or triplet optimal feature selection. The optimal feature subset (x) is stored in a pixel learn database. The data file may be any of a number of local or global pixel databases. As additional ROI and non-ROI selections are made by the user, the optimal feature subset (x) is re-compiled for the entire data file either local or global. Any local and global database to which pixel processing results are concatenated also undergoes the combinatorial optimization algorithm for a refinement of the resident optimal feature subset.

The next step is the selection of the classification algorithm 606 in which an appropriate mapping function is selected that transforms the optimal feature subset (x) into a discrete class label (y). The mapping function is implemented in the form of a classifier. Whereas any classifier known in the art can be employed, two classification algorithms are implemented for their simplicity, transparency, and versatility in pattern learning and discrimination. The two classifiers are multivariate Gaussian (MVG) and Gaussian mixture model (GMM).

The GMM models each class-conditional feature probability density
p(x|y)
as a mixture of Gaussians as shown below:

$$p(x \mid y = i) = \sum_{n=1}^{M_g} g_{ni} N\left(x, \mu_{ni}, \sum_{ni}\right)$$

where $$N\left(x, \mu_{ni}, \sum_{ni}\right) = \frac{1}{\sqrt{(2\pi)^K |\sum_{ni}|}} \exp\left(-0.5(x - \mu_{ni})^t \sum_{ni}^{-1} (x - \mu_{ni})\right)$$

where $M_g$ represents the number of Gaussian mixtures that models p(x|y). The default value for the number of Gaussian mixtures is three; however, the invention is not so limited and any number of mixtures is within the scope of the invention. The number of Gaussian mixtures is not greater than the number of exemplars in each class. For example, if the user makes three ROI selections and three non-ROI selections, then the maximum possible $M_g$ is three. Preferably, the number $M_g$ is less than the number of selections by at least an order of magnitude.

Further in the above equation, K is the feature dimension, $g_{ni}$ is the prior probability associated with the nth mixture for class i, $\mu_{ni}$ is the mean vector (centroid) of the nth mixture for the ith, $(\ )^t$ is the transpose operator, and $\Sigma_{ni}$ is the covariance matrix of the nth mixture for the ith class.

The MVG classifier is a version of GMM where $M_g=1$. In other words, GMM consists of multiple MVGs. MVG parameters consist of a mean vector and covariance matrix for each class, ROI or non-ROI. MVG is advantageous because the learning requires no iterative optimization as in GMM because of the existence of a closed-form solution. The exponent in the above equation called the Mahalanobis distance (r) for the ith class is $$r_i = (x - \mu_i)^t \sum_{i}^{-1} (x - \mu_i)$$

The Mahalanobis distance is computed for the feature vector of each pixel and the feature vector is classified by measuring the Mahalanobis distance from the feature vector to the mean vector (μ) and assigning the feature vector to the class for which the Mahalanobis distance is minimum. The feature vector for each pixel is annotated with the class label, for example 1 for ROI and 0 for non-ROI.

The log-likelihood ratio (LLR) between two classes, ROI and non-ROI is
$M_i$-$M_j$
The LLR controls the classifier threshold. The LLR threshold is 0 for neutrality and positive for the ROI class and negative for the non-ROI class assuming non-ROI-to-ROI ordering.

MVG models each class-conditional feature distribution in terms of its mean vector ($\mu_{ni}$) and covariance matrix ($\Sigma_i$) that measures the spread around the centroid. For each unknown feature vector, MVG computes the normalized distance between the unknown feature vector and the centroid of each class.

Figure 7A:
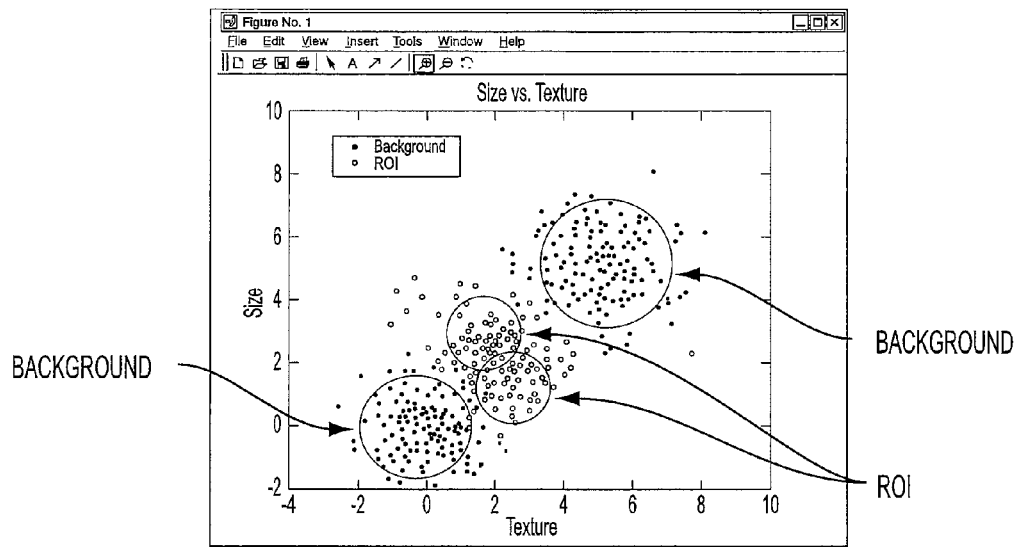
FIG. 7a is a depiction of an example of a multi-modal feature distribution.
Figure 7B:
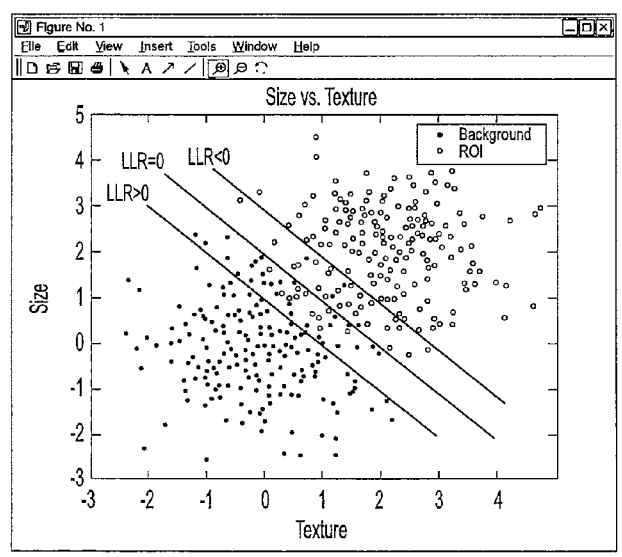
FIG. 7b is a depiction of an example of a unimodal feature distribution.

Selection of the classification algorithm 606 is performed automatically or manually. The user may select an algorithm manually from a graphical user interface (GUI). Alternatively, automatic selection of the classification algorithm is data dependent and involves a recommendation engine. The recommendation engine is an algorithm that examines the feature distribution and recommends the MVG classifier for unimodal feature distributions and the GMM classifier if the feature distribution is multimodal. In short, the learning algorithm that is suited for the underlying feature distribution is selected. FIG. 7 illustrates a simple example. If the actual feature distribution looks multi-modal as in FIG. 7a, GMM is the preferred classifier and the number of clusters determines the number of Gaussian mixtures to be used in representing each class conditional feature distribution. If the actual feature distribution looks unimodal as in FIG. 7b, MVG is the preferred classifier. The recommendation engine also estimates the most appropriate number of modes for the GMM classifier. As shown in FIG. 7a, there are two modes for each class.

As can be seen from above, there are several inputs for the "PIXEL LEARN" processing option, which will now be summarized. The inputs include the image file, which is typically a .jpg or .tif file type. Another input is the N×3 array for identifying pixel locations and their corresponding classification indices selected manually by the user for N number of selections. Another input includes various processing parameters. These processing parameters are stored in a 1×5 row vector wherein the first parameter is the minimum region area in pixels. The user will input the minimum region area based on a number of considerations including laser spot constraints and minimum cell size for single cell capture capability. The second parameter input is the classifier selection. For example, if the user manually inputs or if the recommendation engine automatically selects MVG as the classifier of choice, the second parameter will include a classifier identification such as "1" for MVG and "2" for GMM. The third parameter is a classifier parameter. This classifier parameter is dependent on the type of classifier selected. For example, for the MVG classifier, the LLR offset is the third parameter input where a positive LLR favors ROI detection. For the GMM classifier, the third parameter input is the number of Gaussian mixtures. The fourth parameter of the 1×5 row vector of processing parameters is the region of influence (M). The region of influence is a block of M×M pixels centered on the pixel location for each pixel location in the N×3 pixel-training array. The block is used to derive the pixel-learn database and is manually inputted or pre-selected for maximum robustness. The last element in the processing parameters is a flag that is reserved for debugging statements. For example, if this parameter is set to "1", then debug statements will be written to a text file. Of course, another input is a file name that is used to concatenate pixel learn data for tissue types for example. The file name input includes both path and file name.

Figure 8A:
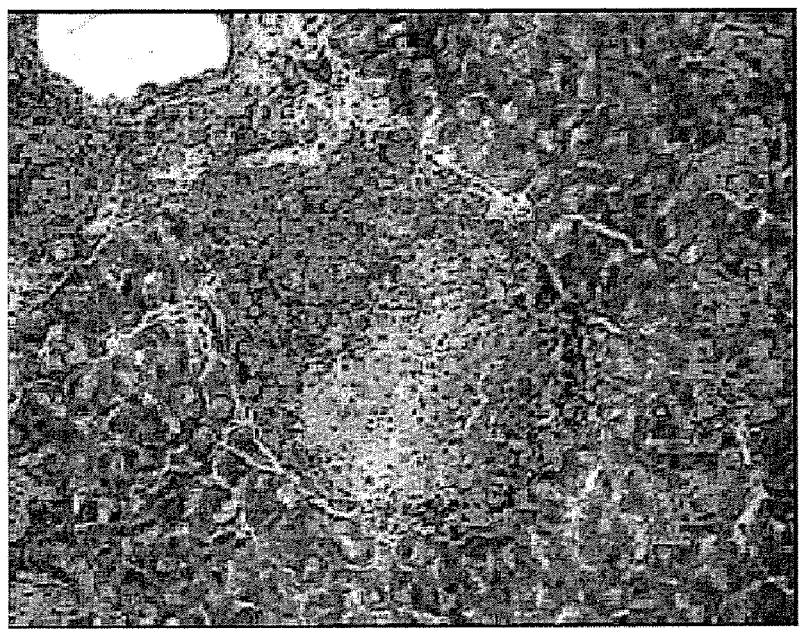
FIG. 8a is one example of a visual output of pixel processing according to the invention.
Figure 8B:
FIG. 8b is one example of a visual output of pixel processing that includes region labeling using color according to the invention.

The output 608 of "PIXEL LEARN" processing is a binary image map for a two-class problem ("1" for non-ROI and "2" for ROI) that is displayed on the computer monitor for user inspection. The output also provides region labeling in which connected pixels of the same class are aggregated into a region and labeled as a ROI or non-ROI region. Each region is numbered and the region label and number are stored in one or more databases. The labeling can be performed in a variety of ways, and color is used to denote a region identification number for easy user identification of regions. FIG. 8a shows the results of pixel processing and the labeling of regions 802 of the binary image map are shown in FIG. 8b.

Additionally, a post-processing step 610 is included to identify potential regions of interest for further processing. For example, in one variation, the binary image map undergoes a post-processing step that determines the size of each region 802. The determination of size of each region assists in the preliminary rejection of a region based on a user-specified size threshold. For example, if the region size is smaller than an average cell size, that region may be discarded from further processing as being considered undesirable for the application such as LCM.

The output of the "PIXEL LEARN" processing option is stored in a local global database 612. The output of "PIXEL LEARN" includes the original image, the labeled image, a boundary structure summarizing classification results, and any error message that may be applicable. The boundary structure that summarizes classification results consists of several fields including a list of pixel locations (x, y), an interior flag, the region area in pixels, the length of the perimeter of a region and the number of boundary pixels. The interior flag is set to one (1) if the boundary of a region belongs to the interior of an object and set to zero (0) otherwise. The list of pixel locations may be sorted, for example by region and by classification. In order to save memory, a polygonal approximation of the external boundary is performed as well.

Figure 9:
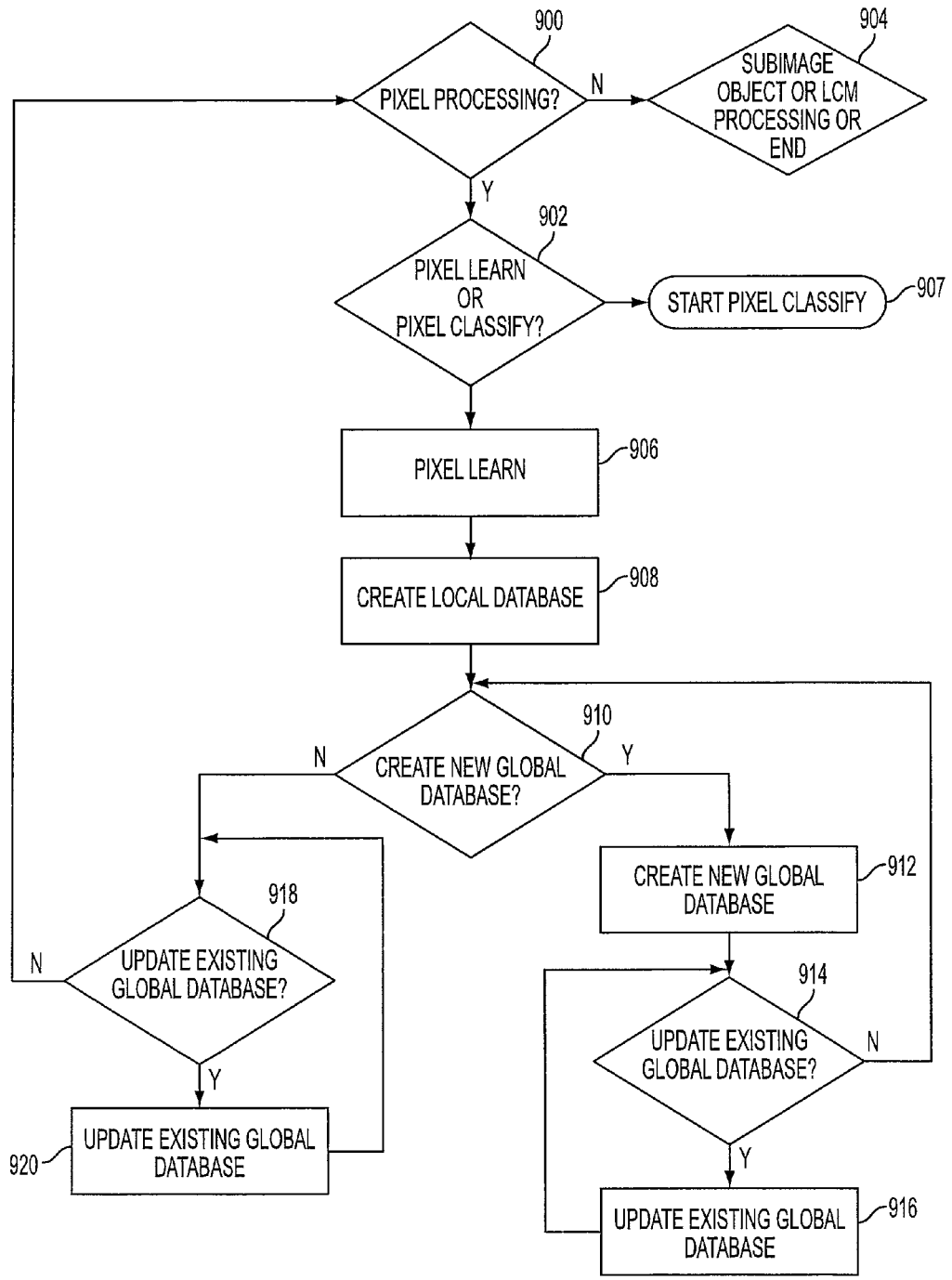
FIG. 9 is a block diagram representation of one example of a method for database management according to the invention.

Database creation and management will now be discussed. As shown in FIG. 4, pixel processing 406 is in electrical communication with various local and global databases 414. This communication with various databases under the "PIXEL LEARN" protocol is illustrated in FIG. 9. Communication with various databases under the "PIXEL CLASSIFY" protocol will be discussed later herewith.

As discussed above, if the user selects pixel processing 900, the user will be prompted at 902 by the GUI to select either the "PIXEL LEARN" 906 or "PIXEL CLASSIFY" 907. If the user does not select pixel processing 900, processing will be directed at 904 to proceed under subimage, object and/or LCM processing as discussed above with respect to FIG. 4. Under "PIXEL LEARN" 906, a local database for a particular image is created 908. For example, local database A is created from pixel processing of image A, which was obtained from a first pancreatic tissue sample for example. The next step is a query at 910 to create a new global database. If yes, a new global database is created 912. Continuing with the example, this new global database, DB1, comprises all the information associated with local database A. This new global database, for example, can be named "pixel data for the first pancreatic tissue sample" in which all the data from all the images of the first tissue sample will be stored. A query to update an existing global database 914 is next. If yes, an existing global database is updated 916 and once again the query 914 is posed to update another existing global database. Continuing with our example, there are no existing global databases to be updated. If no, the query 804 is posed to create another global database. In our example, another global database, DB2 is created 912, for example, and named "pixel data for all pancreatic tissue samples" in which all pixel data associated with all pancreatic tissue samples will be stored. Since in the example there are no existing databases to update 914, 918 and no new global databases to create 910, a query for pixel processing 900 is posed. If pixel processing 900 is desired for another image, the user selects between the "PIXEL LEARN" and "PIXEL CLASSIFY" at 902 once again for the next image to be processed. If pixel processing 900 is not desired, the classification may stop after pixel processing or proceed with subimage, object processing and/or LCM 904. To illustrate the concatenation of databases in this example, another image B but of different location of the same first tissue sample is obtained and processed under "PIXEL LEARN" 906. A local database, database B, is created for image B at 908. At 910, the user is prompted to create a new global database. Using the example, two global databases, DB1 and DB2, have already been created. If it is not desired to create new global databases, the next step is a query 918 to update existing global databases. An existing global database is updated at 920. In the example, data from image B that is resident in database B is used to update existing database DB1. It makes sense to update DB1 since image B is of the first pancreatic tissue sample and data from image B is concatenated to global database DB1, which is called "pixel data for the first pancreatic tissue sample." Now global database DB1 comprises data of local databases A and B. Once again at 918, another existing database may be updated. Using the example, DB2, which is the database for all pancreatic tissue samples, can be selected and updated 920. Likewise DB2 is concatenated with data from database B such that DB2 comprises data of both A and B. Again, a query to proceed with pixel processing is made at 900. As can be seen in the example, with each "PIXEL LEARN" process an updated database grows as more and more parameters are acquired. Updating a database 612 includes not only a concatenation of data but also a re-evaluation of the newly aggregated data. This re-evaluation is performed automatically by an update module and includes a re-ranking of features and a re-selection of the optimal feature subset. Other actions performed in the updating of a database include dimension reduction and an estimation of learning algorithm parameters. The updating of a database is repeated with each new concatenation so that the underlying image algorithms become more intelligent as they age. The databases are updated to reflect the latest changes in tissue samples or staining methods such that when they are retrieved they are suitable for use with processing at the same or next level of abstraction. From "PIXEL LEARN" the user may select to proceed with LCM if it so desired.

The "PIXEL CLASSIFY" option will now be discussed. "PIXEL CLASSIFY" employs data accumulated and stored in various databases from one or more learning stages such as the "PIXEL LEARN" stage. As discussed above, during "PIXEL LEARN" the user provides truth annotations, for example ROI and non-ROI selections for representative images using GUI controls. Then, the system discriminates ROIs from non-ROIs using classifiers. During the learning stage, all the parameters and feature values associated with pattern learning are stored for each image being investigated in one or more database such as local and global databases. The data from "PIXEL LEARN" is also concatenated to one or more global databases as discussed above with respect to FIG. 9. During "PIXEL CLASSIFY" the system utilizes the learned parameters stored in one or more databases to perform automatic classification of regions as being ROIs or non-ROIs. As the databases grow with time as more data is acquired during "PIXEL LEARN," "PIXEL CLASSIFY" improves with age. The "PIXEL CLASSIFY" operating mode is designed for high-throughput batch processing with the human operator inspecting the processed results for final decision.

Referring back to FIG. 5, after "PIXEL CLASSIFY" is selected as the pixel processing option at 510, "PIXEL CLASSIFY" will start 514 by prompting the user via the GUI to load an appropriate database 524 if one is available. If no appropriate database is available, the user will be directed to start "PIXEL LEARN" 512. A pull-down menu on the GUI provides a list of appropriate local and global databases to be selected 526 by the user under "PIXEL CLASSIFY." Typically, the available databases are local or global databases created during "PIXEL LEARN" and matched for the particular image at hand. For example, if the image is a pancreatic tissue sample, the user may select any local or global pancreatic tissue database at the pixel level of abstraction at 526. The next step is to run the classification 528 under "PIXEL CLASSIFY."

Figure 10:
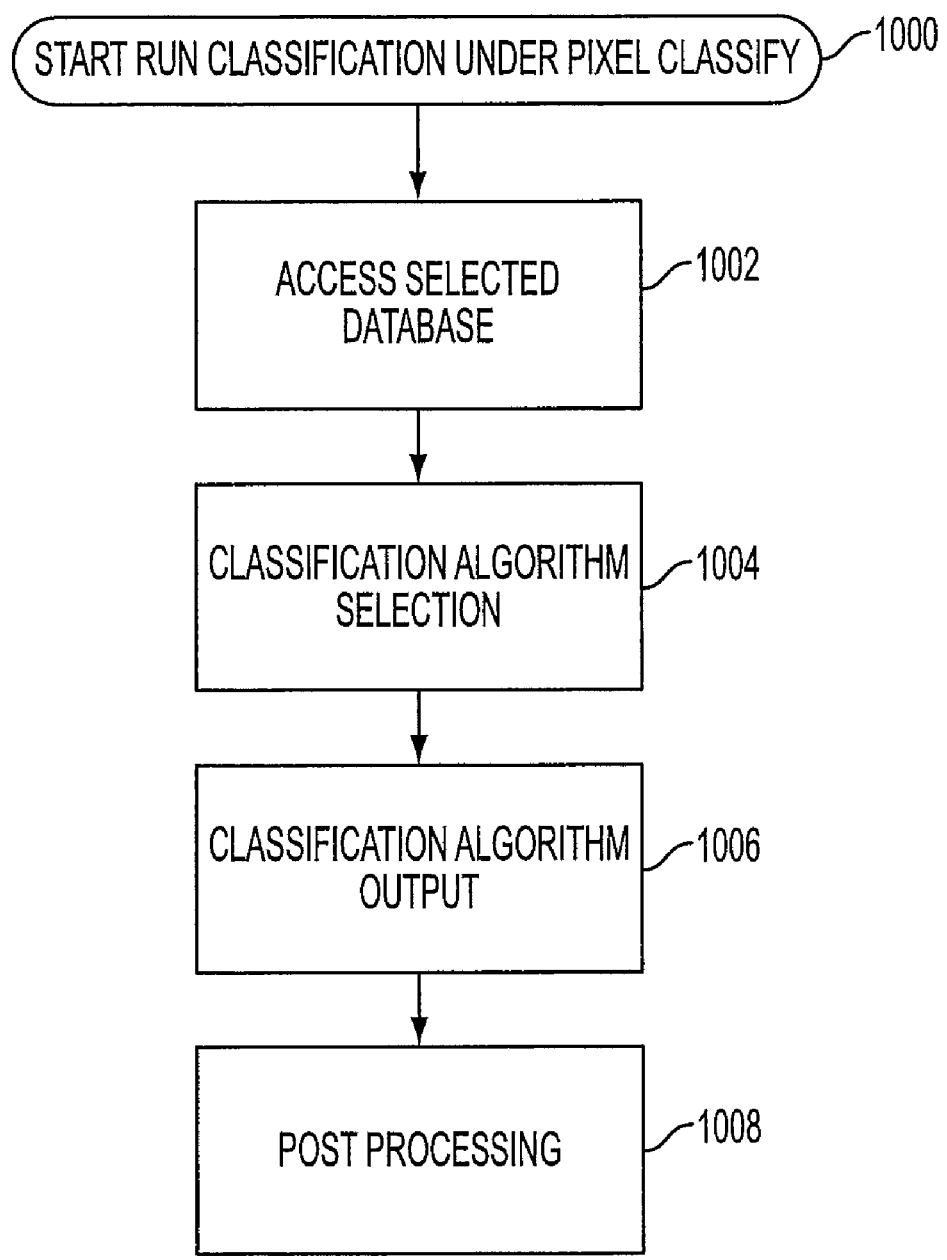
FIG. 10 is a block diagram representation of one method of run-classification under the "PIXEL CLASSIFY" processing option according to the invention.

Running the classification under "PIXEL CLASSIFY" is depicted in FIG. 10. After the start of "run classification" 1000, the database that was selected at 526 is accessed 1002 for critical algorithmic parameters and for the optimal feature subset. The selected database has already been updated at 520. Hence, the database has undergone a ranking or re-ranking of features and selection or re-selection of the optimal feature subset. Therefore, these values are ready for use with the classification algorithm that is selected at 1004. In "PIXEL CLASSIFY," the classification algorithm is selected automatically. Automatic selection of the classification algorithm is data dependent and involves a recommendation engine. The recommendation engine is an algorithm that examines the feature distribution and recommends the MVG classifier for unimodal feature distributions and the GMM classifier if the feature distribution is multimodal. The recommendation engine also estimates the most appropriate number of modes for the GMM classifier.

The output 1006 of "PIXEL CLASSIFY" is the same as the output of "PIXEL LEARN." The output 1006 of "PIXEL CLASSIFY" processing is a binary image map for the two-class problem ("1" for non-ROI and "2" for ROI) that is displayed on the computer monitor for user inspection. The output also provides region labeling in which connected pixels of the same class are aggregated into a region and labeled as a ROI or non-ROI region. Each region is numbered and the region label and number are stored in one or more databases. The labeling can be performed in a variety of ways, and color is used to denote a region identification number for easy user identification of regions.

The final step of "run classification" is post-processing 1008. Post-processing 1008 under "PIXEL CLASSIFY" is the same as post-processing 610 under "PIXEL LEARN." The post-processing step 1008 identifies potential regions of interest for further processing. For example, in one variation, the binary image map undergoes a post-processing step that determines the size of each region. The determination of size of each region assists in the preliminary rejection of a region based on a user-specified size threshold. For example, if the region size is smaller than an average cell size, that region may be discarded from further processing as being considered undesirable for the application such as LCM.

The output of "PIXEL CLASSIFY" includes the original image, the labeled image, a boundary structure summarizing classification results, and any error message that may be applicable. The boundary structure that summarizes classification results consists of several fields including a list of pixel locations (x, y), an interior flag, the region area in pixels, the length of the perimeter of a region and the number of boundary pixels. The interior flag is set to one (1) if the boundary of a region belongs to the interior of an object and set to zero (0) otherwise. The list of pixel locations may be sorted, for example by region and by classification. In order to save memory, a polygonal approximation of the external boundary is performed as well.

Upon viewing the output of either the "PIXEL LEARN" or "PIXEL CLASSIFY" options, the user determines whether to proceed to LCM along line 416 in FIG. 4 or along line 418 to the next level of abstraction, subimage processing or object processing. If the user determines that the output binary image map is satisfactory and does not include any false accepts, then the user selects LCM from the GUI. If the tissue slide is loaded in the LCM device, the processor will automatically position the laser at coordinates corresponding to ROIs from the binary image map. Once positioned, the laser is activated for LCM and the ROIs are transferred to the LCM transfer film and removed from the tissue sample. If the user determines that the output binary image map is not satisfactory due to a more complex image, for example, the user then selects from the GUI to proceed to subimage processing 408. Alternatively, the user may select to bypass subimage and proceed to object processing 410 prior to LCM 412.

Referring now to FIG. 1, subimage processing will now be discussed. Subimage processing overcomes difficulties associated with the output of pixel processing. For example, subimage processing will differentiate between two classes, ROI and non-ROI, with similar color by extracting additional features related to texture over a swath of the image that is larger than a single pixel. At the start of subimage processing 1100, if a data image file is not already loaded from the previous step of pixel processing, the user is prompted by the GUI to retrieve a image data file corresponding to the current image that has undergone pixel processing for user observation 1101. The image, typically in .jpg or .tff file format is inputted along with the labeled image from pixel processing at 1101. At the same time, in one variation, the pixel processing data file corresponding to the image at hand is saved as a subimage processing data file for the same image. Subimage processing stores data to this newly created subimage processing data file. Typically, the user views the raw image of the tissue sample on the computer monitor. Before proceeding with the classification, the user selects one of two subimage processing protocol options at 1102 from the GUI. One of the subimage processing protocols is "SUBIMAGE LEARN" 1104 and the other is called "SUBIMAGE CLASSIFY" 1106. The user chooses "SUBIMAGE CLASSIFY" 1106 if an existing database is to be employed and applied to the current image for automated classification. The "SUBIMAGE CLASSIFY" option 1106 will be discussed in detail hereinbelow. The "SUBIMAGE LEARN" 1104 option is chosen if the user does not wish to employ an existing database and apply it to the current image. "SUBIMAGE LEARN" 1104 enables the user to create a new subimage database for the current image. The subimage database for the current image is concatenated to a variety of other new or existing, local or global type databases.

"SUBIMAGE LEARN" 1104 is processing along the learning and automatic classification axis or second dimension processing as opposed to the variable abstraction axis discussed above. "SUBIMAGE LEARN" and the second dimension of learning and automatic classification permits the system to become more intelligent with time as data and processing results from the "SUBIMAGE LEARN" stage are stored in various databases.

In general, "SUBIMAGE LEARN," as with any of the learning stage, requires interactive processing with end user participation in which the end user participates by providing a predetermined number, preferably at least three, of ROI and non-ROI selections all at the subimage level of abstraction. Then, the system takes over and creates individual trained databases, which are then concatenated to form local or global databases for use with the "SUBIMAGE CLASSIFY" option 1106, which is automated and requires little end user participation. The "SUBIMAGE LEARN" 1104 option will now be discussed in greater detail.

Figure 12:
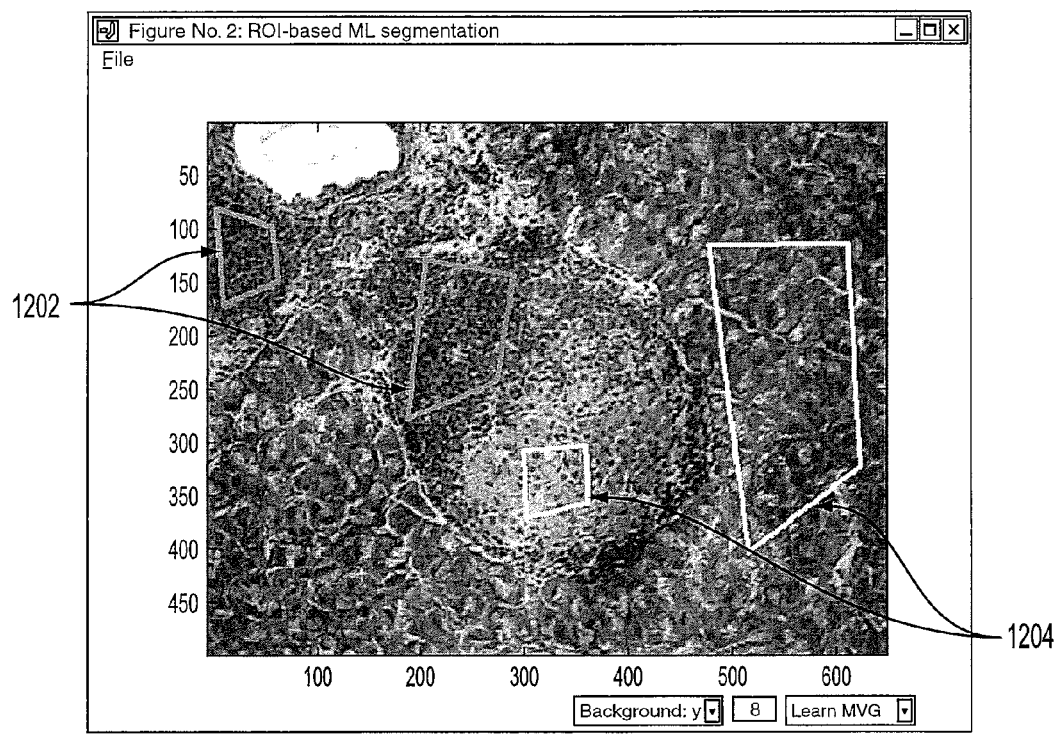
FIG. 12 is an one example of a visual output during subimage processing that includes polygonal ROI and non-ROI segments according to the invention.

In "SUBIMAGE LEARN" 1104 under the subimage processing protocol 1100, the user selects at least one subimage region of interest (ROI) 1108 from the image viewed on the computer monitor using a mouse or some other pointing device coupled to the computer. Preferably, the user selects three or more subimage ROIs. The user is also prompted to select at least one subimage non-ROI 1108. Preferably, the user also selects three or more subimage non-ROIs. Each subimage selection is a selection of a region larger than one pixel. Generally, the subimage region is equal to or larger than a predetermined minimum size that is inputted by the user. This predetermined minimum size for a subimage selection is preferably 4 to approximately 32 pixels. The predetermined minimum can be tailored according to various tissue types undergoing study. In one variation, the user makes a subimage selection using a GUI interface to draw a polygonal shape. The polygonal shape is drawn by clicking on an area of the image with a pointing device and then dragging the pointer to designate a polygonal subimage ROI or non-ROI segment. The maximum size of the ROI and non-ROI subimage segment is at the user's discretion so long as it is a subset of the entire image and does not overlap with other ROI or non-ROI polygonal region selections. Once a subimage ROI is designated on the image, for example, by a polygonal shape, that designation is indicated in a color that is different from a subimage non-ROI designation on the same image for easy user identification. The user-specified subimage regions are non-overlapping regions as shown in FIG. 12. For example, the subimage ROI polygons 1202 are magenta in color and the subimage non-ROI polygons 1204 are yellow.

With the subimage selections, the image data file is annotated with the additional information obtained from the subimage selections at 1110. Each subimage selection or exemplar annotates the pixel output vector of all the pixel locations associated with the subimage region with another value that identifies the type of selection, ROI or non-ROI, for the pixel locations included in the subimage region. This annotation is performed for the entire L×M matrix for the image. The annotation to each vector is a binary value such that, for example, the number "1" is used for non-ROI selections and the number "2" is used for non-ROI selections. The matrix is stored in the subimage data file associated with the image 1112.

Figure 13:
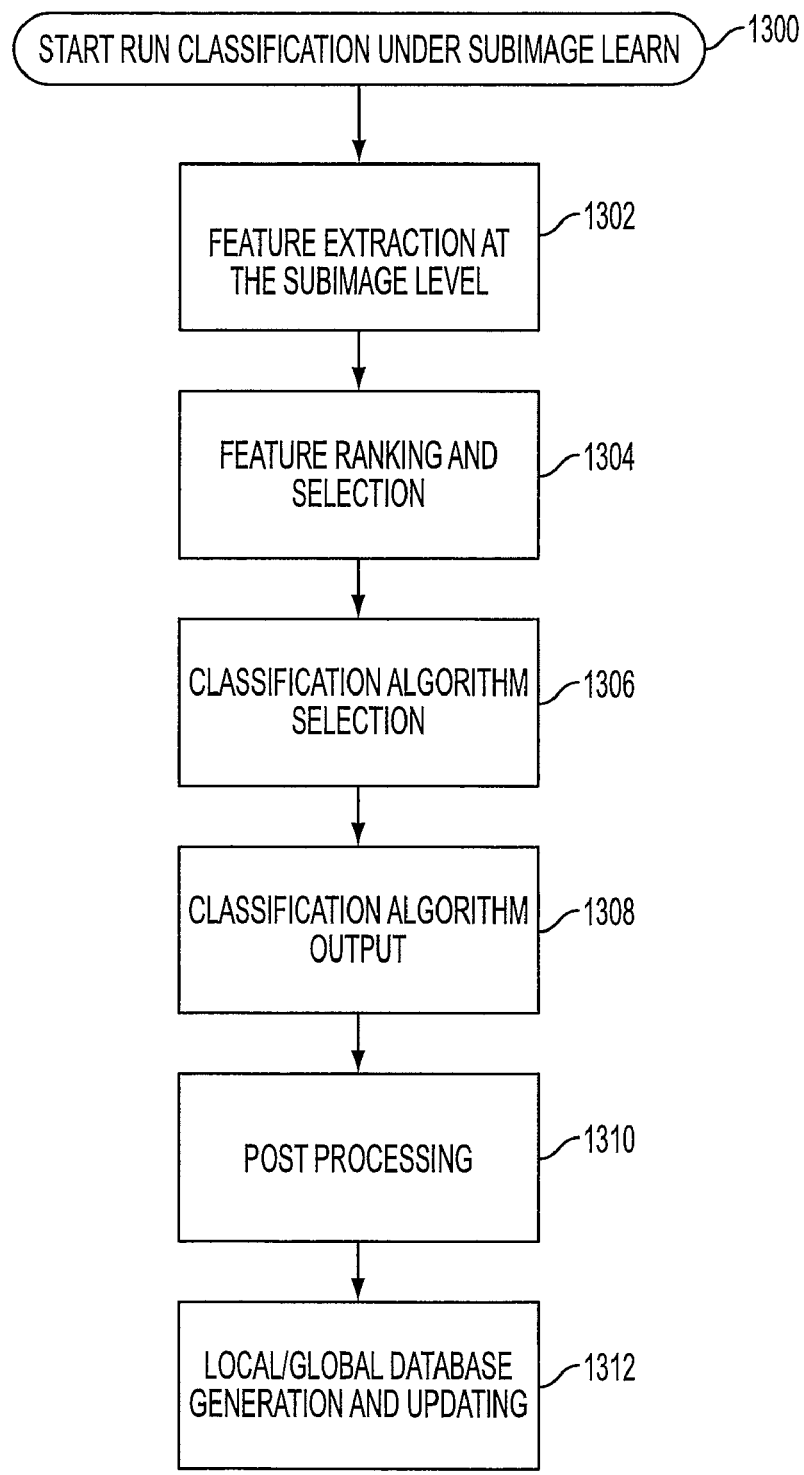
FIG. 13 is an is a block diagram representation of a method of run-classification under the "SUBIMAGE LEARN" processing option according to the invention.

The next step is to run the classification 1114. Referring now to FIG. 13, there is depicted the steps comprising run classification under "SUBIMAGE LEARN." At the start of classification 1300, the first step is feature extraction 1302 at the subimage level. Feature extraction 1302 at the subimage level differs from feature extraction at the pixel level performed during pixel processing. In subimage processing, feature extraction uses pixel results to reduce the problem dimension by extracting a different set of features such as texture-related information at a subimage level selected by user. The following table lists the types of features that are extracted at the subimage level.

| | TABLE OF SUBIMAGE-LEVEL FEATURES |
|---|---|
| 1 | Mean intensity of each subimage |
| 2 | Standard deviation of subimage pixels |
| 3 | Coefficient of variation |
| 4 | (Maximum pixel intensity-minimum pixel intensity)/standard deviation |
| 5 | The fraction of low-frequency energy as defined by the discrete cosine transformation (DCT) |

TABLE OF SUBIMAGE-LEVEL FEATURES

| | |
|---|---|
| 6 | DC energy fraction, which is the mean energy of each subimage (mean of R, G, and B) |
| 7 | Mean/standard deviation of DCT coefficients in the LL sub-band quadrant (L = low frequency, H = high frequency) |
| 8 | Mean/standard deviation of DCT coefficients in the LH sub-band quadrant |
| 9 | Mean/standard deviation of DCT coefficients in the HL sub-band quadrant |
| 10 | Mean/standard deviation of DCT coefficients in the HH sub-band quadrant |
| 11 | Mean of vertical difference in intensity |
| 12 | Mean of horizontal difference in intensity |
| 13 | Standard deviation of vertical difference in intensity |
| 14 | Standard deviation of horizontal difference in intensity |
| 15 | Coefficient of variation of vertical difference in intensity |
| 16 | Coefficient of variation of horizontal difference in intensity |

The above features are selected to characterize each subimage in terms of trend, texture, normalized variation and normalized color.

The above features are repeated as applied to the RGB space such that the final analysis results are based on 48 features. These 48 features include the above 1-16 features derived or calculated from the red space, the above features repeated and derived or calculated from the green space (17-32), and the above features repeated and derived or calculated from the blue space (33-48). In one variation, in addition to the above features being repeated for the RGB space, they are also repeated for the HSV space, such that the above features are repeated for the hue space, saturation space and intensity space. As a result, a total of 96 features are extracted in such variation.

In yet another variation, the following table lists another set of features that are extracted at the subimage level.

TABLE OF SUBIMAGE-LEVEL FEATURES

| | |
|---|---|
| 1 | Mean |
| 2 | Standard deviation |
| 3 | Mean color differences in the horizontal direction |
| 4 | Standard deviation of color differences in the horizontal direction |
| 5 | Mean color differences in the vertical direction |
| 6 | Standard deviation of color differences in the vertical direction |

The above features are repeated as applied to the RGB space such that the final analysis results are based on 18 features. The above 18 features maximize computational speed while at the same time prove to be reasonably effective as compared to the previous 48 features. In one variation, the user selects which set of features from a library set to employ for a given situation, which of course is dependent on the complexity of the image to be classified.

The features are extracted from the image, compiled in vector form and stored with the associated subimage data file. The next step is feature ranking 1304 in which the subimage features are ranked according to their effectiveness in discriminating ROIs. Feature ranking is performed in substantially the same way as in pixel processing by using any combinatorial optimization algorithm known in the art such as add-on or forward-backward ranking algorithm to first iteratively rank each single subimage feature (singlet) from best feature to worst feature. Feature performance is based on the degree of successful detection of subimages that fall into a ROI-annotated region that is made by the user and reserved for performance testing. For example, if a user selects four ROI subimage regions, two ROI selections will be reserved to test the performance of features obtained from the other two ROI selections. Each singlet will be then ranked accordingly using the combinatorial optimization algorithm.

The combinatorial optimization algorithm proceeds to then iteratively rank pairs of features (doublets). For example, the first ranked singlet will be paired with another feature and the performance of both features in combination will be ranked against other doublets. The combinatorial optimization algorithm proceeds to then iteratively rank sets of three features (triplets). For example, the first ranked doublet will be combined with another feature to form a triplet of features, which will be ranked against other triplets. The algorithm ranks singlets, doublets, triplets, quadruplets and so on until the improvement in performance for detecting a ROI reaches a predetermined value or point of diminishing returns at which point a feature singlet, doublet or triplet is extracted. For example, the highest ranked triplet may provide only a small percent increase in performance over the highest ranked doublet in which case, the doublet would be the selected feature combination to be employed in the next step in classification. This estimation of the point of diminishing returns advantageously enhances real-world performance by avoiding data-overfitting or memorization during learning. The result of the optimization algorithm is a subimage feature subset (x) e.g., a singlet, doublet, or triplet optimal subimage feature selection. The optimal subimage feature subset (x) is stored in the subimage data file. The data file may be any of a number of local or global databases.

The next step is the selection of the classification algorithm 1306 in which an appropriate mapping function is selected that transforms the optimal subimage feature subset (x) into a discrete class label (y). The mapping function is implemented in the form of a classifier. Classification algorithm selection 1306 is performed in the same way as in pixel processing. Selection of the classification algorithm 1306 is performed automatically or manually. The user may select a classification algorithm manually from a GUI interface that provides a list of any number of suitable algorithms. Typically, the selection involves a choice between GMM and MVG. Alternatively, automatic selection of the classification algorithm is data dependent and involves a recommendation engine. The recommendation engine is an algorithm that examines the subimage feature distribution and recommends the MVG classifier for unimodal feature distributions and the GMM classifier if the feature distribution is multimodal. If the actual feature distribution looks multi-modal, GMM is the preferred classifier and the number of clusters determines the number of Gaussian mixtures to be used in representing each class conditional feature distribution. If the actual feature distribution looks unimodal, MVG is the preferred classifier. The recommendation engine also estimates the most appropriate number of modes for the GMM classifier.

As can be seen from above, there are several inputs for the "SUBIMAGE LEARN" processing option, which will now be summarized. The inputs include the image file, which is typically a .jpg or .tif file type, and the labeled image from pixel processing. Another input is the N×3 array for identifying pixel locations and their corresponding classification indices selected manually by the user for all of the pixels in each subimage selection. Another input includes various processing parameters. These processing parameters are stored in a 1×5 row vector wherein the first parameter is the minimum subimage region size in pixels. The user will provide the minimum region area based on a number of considerations including laser spot constraints and minimum cell size for single cell capture capability. The second parameter is the actual size of the subimage selected by the user. The third parameter input is the classifier selection. For example, if the user manually inputs or if the recommendation engine automatically selects MVG as the classifier of choice, the second parameter will include a classifier identification such as "1" for MVG and "2" for GMM. The fourth parameter is a classifier parameter. This classifier parameter is dependent on the type of classifier selected. For example, for the MVG classifier, the LLR offset is the fourth parameter input where a positive LLR favors ROI detection. For the GMM classifier, the fourth parameter input is the number of Gaussian mixtures. The fifth and last element in the processing parameters is a flag that is reserved for debugging statements. For example, if this parameter is set to "1", then debug statements will be written to a text file. Of course, another input is a file name, which is used to concatenate subimage learn data for particular tissue types. The file name input includes both path and file name.

Figure 14A:
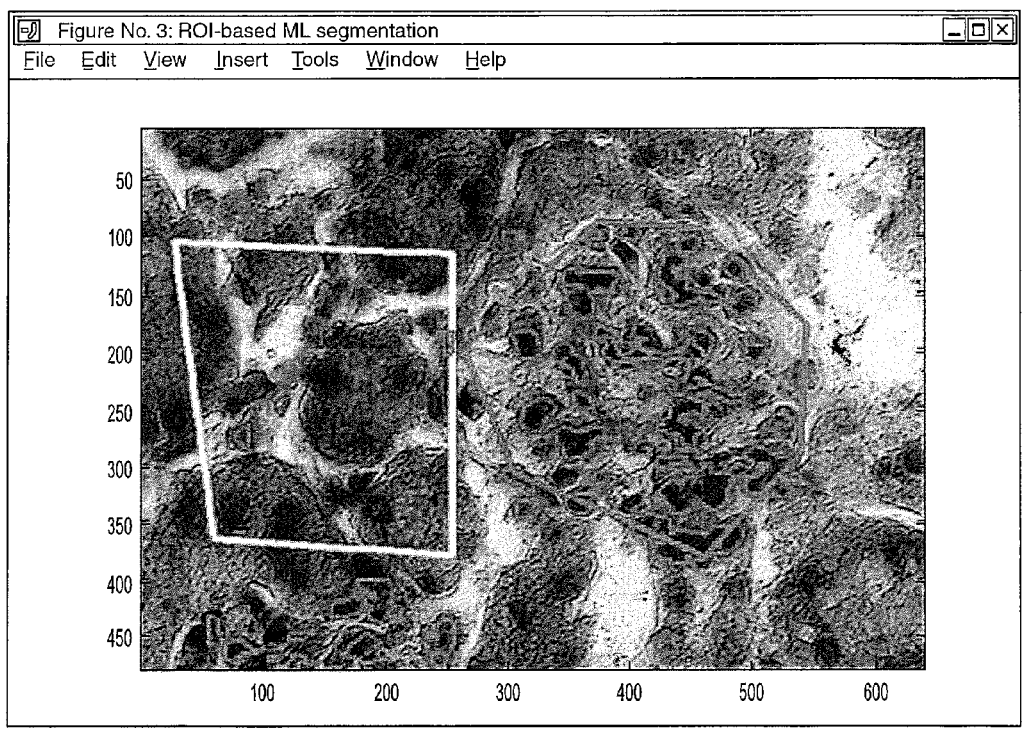
FIG. 14a is one example of a visual output of subimage processing according to the invention.
Figure 14B:
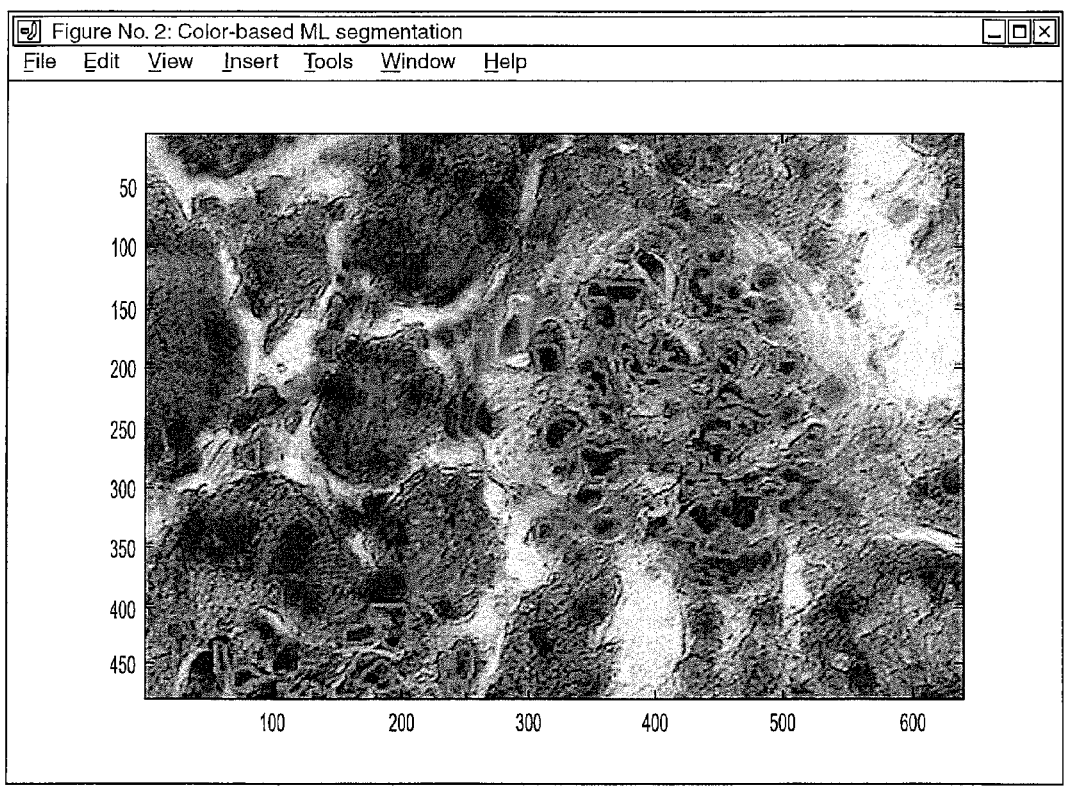
FIG. 14b is one example of a visual output of pixel processing according to the invention.

The output 1308 of "SUBIMAGE LEARN" processing is a binary subimage map for a two-class problem ("1" for non-ROI and "2" for ROI) that is displayed on the computer monitor for user inspection. The output also provides region labeling in which connected pixels of the same class are aggregated into a region and labeled as a ROI or non-ROI region. Each region is numbered and the region label and number are stored in one or more databases. The labeling can be performed in a variety of ways, and color is used to denote a region identification number for easy user identification of regions. FIG. 14a shows the results of subimage processing. FIG. 14b shows the results of pixel processing alone for the same image.

Additionally, a post-processing step 1310 is included to identify potential regions of interest for further processing. For example, in one variation, the binary image map undergoes a post-processing step that determines the size of each region. The determination of size of each region assists in the preliminary rejection of a region based on a user-specified size threshold. For example, if the region size is smaller than an average cell size, that region may be discarded from further processing as being considered undesirable for the application such as LCM. Also, during the post-processing step 1310, a false accept rejection is performed. The results of subimage processing and pixel processing are combined to create a cleansed binary image map.

The output of the "SUBIMAGE LEARN" processing option is stored in a local database. The output of "SUBIMAGE LEARN" includes the original image, a further refined and labeled image, a boundary structure summarizing classification results, and any error message that may be applicable. The boundary structure that summarizes classification results consists of several fields including a list of pixel locations (x, y) and their corresponding classification, an interior flag, the region area in pixels, the length of the perimeter of a region and the number of boundary pixels. The interior flag is set to one (1) if the boundary of a region belongs to the interior of an object and set to zero (0) otherwise. The list of pixel locations may be sorted, for example by region and by classification.

Database creation and management 1312 is the same as that discussed above with respect to pixel processing and described in FIG. 9. Basically, database management and creation 1312 for subimage processing is the same as shown in FIG. 9 wherein the word "pixel" is replaced with the word "subimage." As shown in FIG. 4, subimage processing 408 is in electrical communication with various local and global databases 414. As additional ROI and non-ROI selections are made by the user when in the "SUBIMAGE LEARN" processing protocol, the optimal subimage feature subset (x) is re-compiled for the entire data file either local or global. Any local and global database to which subimage processing results are concatenated also undergoes the combinatorial optimization algorithm for a refinement of the resident optimal subimage feature subset.

The "SUBIMAGE CLASSIFY" option will now be discussed. "SUBIMAGE CLASSIFY" employs data accumulated and stored in various databases from one or more learning stages such as the "SUBIMAGE LEARN" stage. As discussed above, during "SUBIMAGE LEARN" the user provides truth annotations, for example ROI and non-ROI subimage selections for representative images using GUI controls. Then, the system discriminates ROIs from non-ROIs using classifiers. During the learning stage, all the parameters and feature values associated with pattern learning are stored for each image being investigated in one or more database such as local and global databases. The data from "SUBIMAGE LEARN" is also concatenated to one or more global databases as discussed above. During "SUBIMAGE CLASSIFY" the system utilizes the learned parameters stored in one or more subimage databases to perform automatic classification of regions as being ROIs or non-ROIs. As the databases grow with time as more data is acquired during "SUBIMAGE LEARN," "SUBIMAGE CLASSIFY" improves with age. The "SUBIMAGE CLASSIFY" operating mode is designed for high-throughput batch processing with the human operator inspecting the processed results for final decision.

Figure 11:
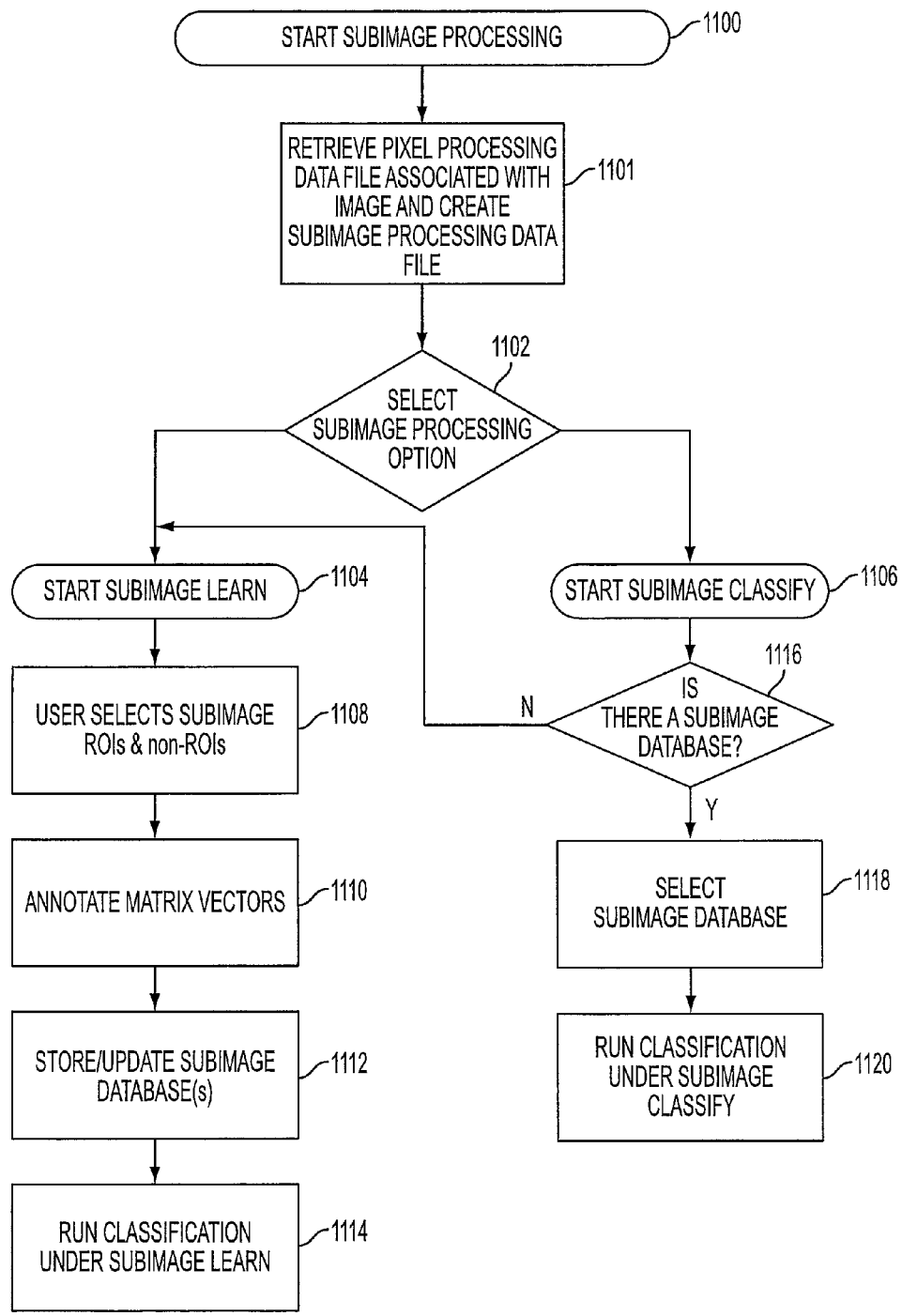
FIG. 11 is a block diagram representation of a method of subimage processing according to the invention.

Referring back to FIG. 11, after "SUBIMAGE CLASSIFY" is selected as the subimage processing option at 1102, "SUBIMAGE CLASSIFY" will start 1106 by prompting the user via the GUI to load an appropriate database 1116 if one is available. If no appropriate database is available, the user will be directed to start "SUBIMAGE LEARN" 1104. A pull-down menu on the GUI provides a list of appropriate local and global databases to be selected by the user under "SUBIMAGE CLASSIFY" 1118. Typically, the available databases are ones created during "SUBIMAGE LEARN" and matched for the particular image at hand. For example, if the image is a pancreatic tissue sample, the user may select any subimage local or global pancreatic tissue database. Of course, the image of the tissue sample is also loaded and displayed on the monitor when the database is selected. The next step is to run the classification under "SUBIMAGE CLASSIFY" 1120.

Figure 15:
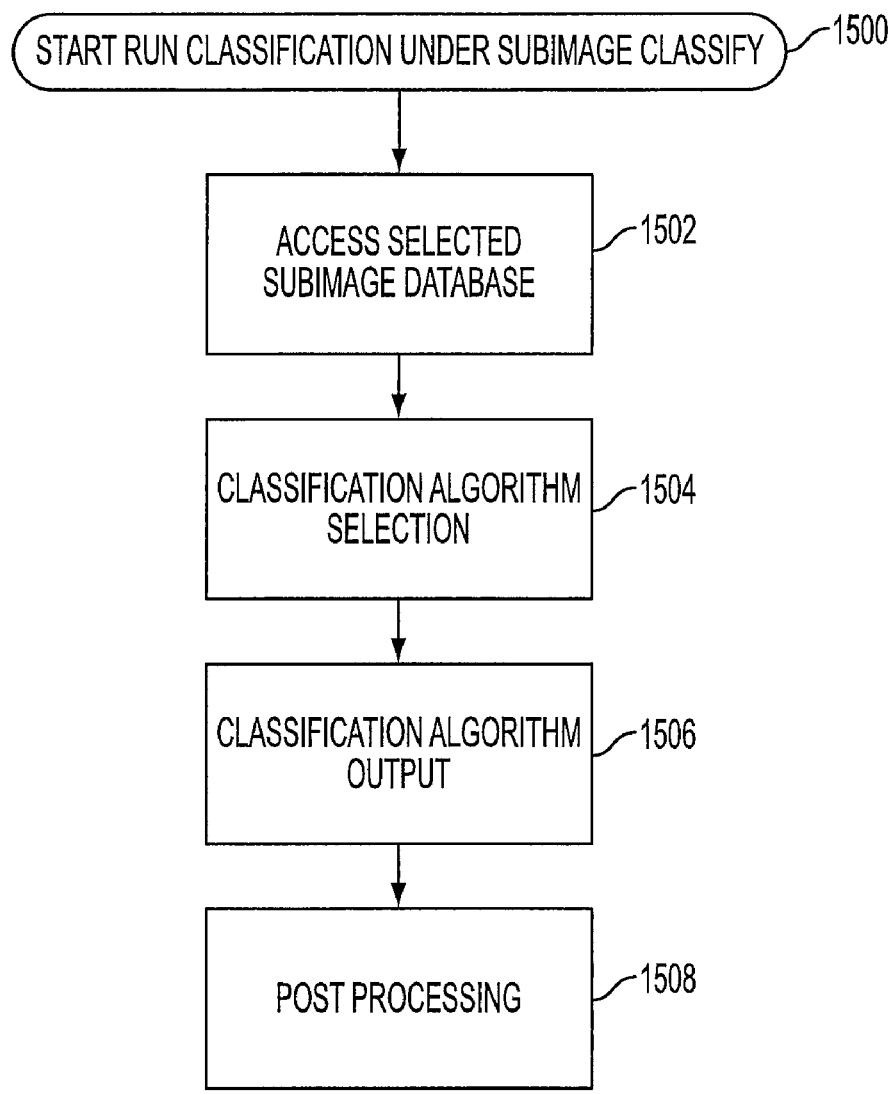
FIG. 15 is a block diagram representation of one method of run-classification under the "SUBIMAGE CLASSIFY" processing option according to the invention.

Running the classification under "SUBIMAGE CLASSIFY" is depicted in FIG. 15. After the start of "run classification" 1500, the database that was selected at 1118 is accessed 1502 for critical algorithmic parameters and for the optimal subimage feature subset. The selected subimage database has already been updated at 1112. Hence, the database has undergone a ranking or re-ranking of features and selection or re-selection of the optimal subimage feature subset. Therefore, these values are ready for use with the classification algorithm that is selected at 1504.

In "SUBIMAGE CLASSIFY," the classification algorithm is selected automatically. Automatic selection of the classification algorithm is data dependent and involves a recommendation engine. The recommendation engine is an algorithm that examines the feature distribution and recommends the MVG classifier for unimodal subimage feature distributions and the GMM classifier if the feature distribution is multimodal. The recommendation engine also estimates the most appropriate number of modes for the GMM classifier.

The output 1506 of "SUBIMAGE CLASSIFY" is the same as the output of "SUBIMAGE LEARN." The output of "SUBIMAGE CLASSIFY" processing is a binary image map for the two-class problem ("1" for non-ROI and "2" for ROI) that is displayed on the computer monitor for user inspection. The output also provides region labeling in which connected pixels of the same class are aggregated into a region and labeled as a subimage ROI or non-ROI region. Each region is numbered and the region label and number are stored in one or more databases. The labeling can be performed in a variety of ways, and color is used to denote a region identification number for easy user identification of regions.

The final step of "run classification" is post-processing 1508. Post-processing under "SUBIMAGE CLASSIFY" is substantially the same as post-processing under "SUBIMAGE LEARN." The post-processing step identifies potential regions of interest for further processing. For example, in one variation, the binary image map undergoes a post-processing step that determines the size of each region. The determination of size of each region assists in the preliminary rejection of a region based on a user-specified size threshold. For example, if the region size is smaller than an average cell size, that region may be discarded from further processing as being considered undesirable for the application such as LCM.

The output of "SUBIMAGE CLASSIFY" includes the original image, the labeled image, a boundary structure summarizing classification results, and any error message that may be applicable. The boundary structure that summarizes classification results consists of several fields including a list of pixel locations (x, y), an interior flag, the region area in pixels, the length of the perimeter of a region and the number of boundary pixels. The interior flag is set to one (1) if the boundary of a region belongs to the interior of an object and set to zero (0) otherwise. The list of pixel locations may be sorted, for example by region and by classification. In order to save memory, a polygonal approximation of the external boundary is performed as well.

Upon viewing the output of either the "SUBIMAGE LEARN" or "SUBIMAGE CLASSIFY" options, the user determines whether to proceed to LCM along line 416 in FIG. 4 or along line 418 to the next level of abstraction which is object processing. If the user determines that the output binary image map is satisfactory and does not include any false accepts, then the user selects LCM from the GUI. If the tissue slide is loaded in the LCM device, the processor will automatically position the laser at coordinates corresponding to ROIs from the binary image map. Once positioned, the laser is activated for LCM and the ROIs are automatically transferred to the LCM transfer film and removed from the tissue sample. If the user determines that the output binary image map is not satisfactory due to a more complex image, for example, the user then selects from the GUI to proceed to object processing 410.

Figure 16:
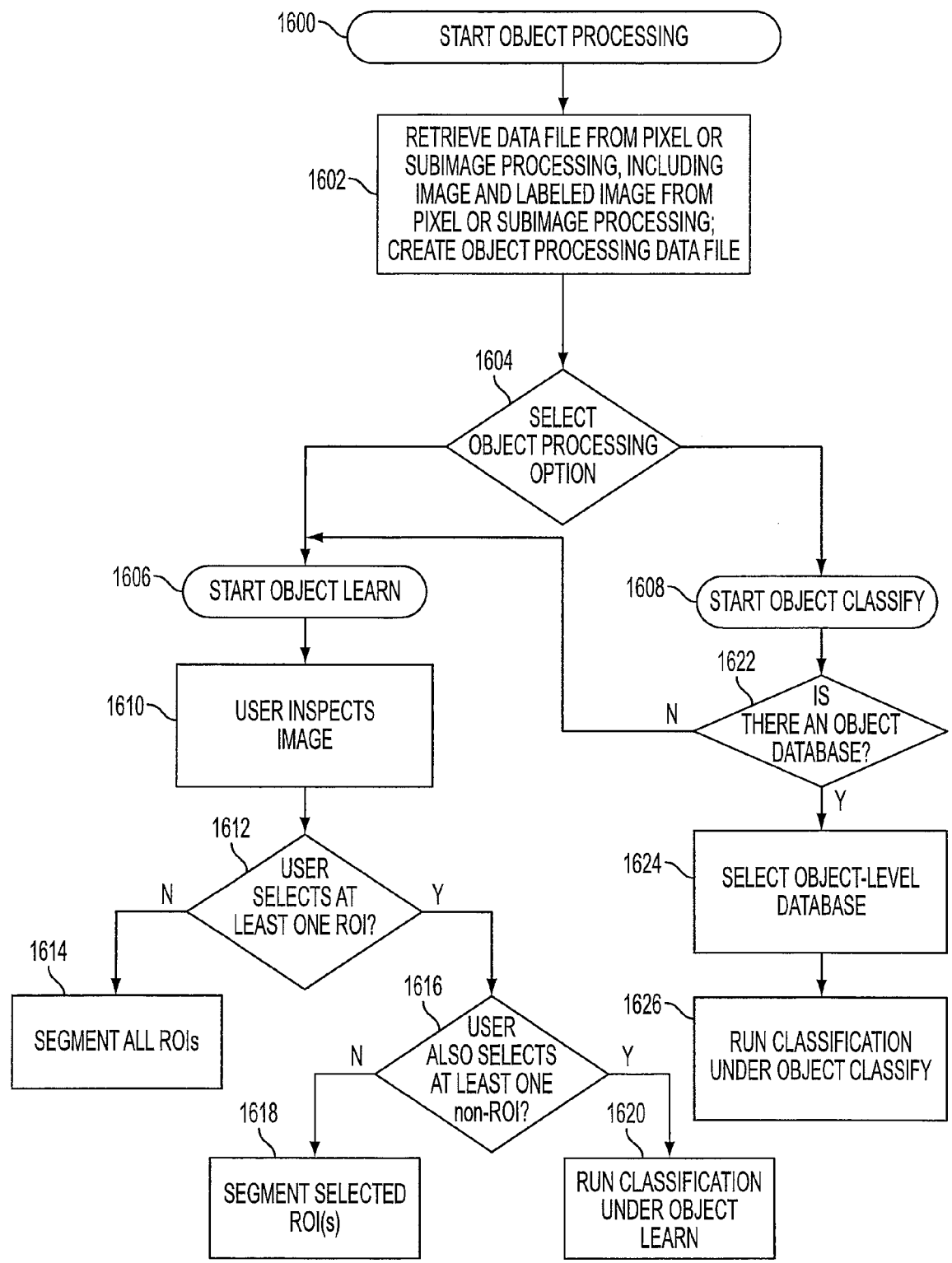
FIG. 16 is a block diagram representation of a method of object processing according to the invention.

Referring now to FIG. 16, object processing which is also called region processing will now be discussed. Object processing overcomes difficulties associated with the output of pixel processing or subimage processing by utilizing texture, morphology and gradient information at an object level. At the start of object processing 1600, if a data image file is not already loaded from the previous step of pixel processing or subimage processing, the user is prompted by the GUI to retrieve an image data file corresponding to the current image that has undergone pixel processing or subimage processing 1602. The image, typically in jpg or .tff file format, is inputted along with the labeled image from pixel processing or subimage processing at 1602. At the same time, in one variation, the pixel processing or subimage processing data file corresponding to the image at hand is saved as an object processing data file for the same image. Object processing stores data to this newly created object processing data file. Typically, the user views the raw image or the labeled image of the tissue sample on the computer monitor. The user selects one of two object processing protocol options at 1604 from the GUI. One of the object processing protocols is "OBJECT LEARN" 1606 and the other is called "OBJECT CLASSIFY" 1608. The user chooses "OBJECT CLASSIFY" 1608 if an existing object database is to be employed and applied to the current image for automated classification. The "OBJECT CLASSIFY" option 1608 will be discussed in detail hereinbelow. The "OBJECT LEARN" 1606 option is chosen to create a new object database or if the user does not wish to employ an existing database and apply it to the current image. "OBJECT LEARN" 1606 enables the user to create a new object database for the current image. The object database for the current image is concatenated to a variety of other new or existing, local or global type databases.

"OBJECT LEARN" 1606 is processing along the learning axis or second dimension processing as opposed to the variable abstraction axis discussed above. "OBJECT LEARN" and the second dimension of learning and automatic classification permit the system to become more intelligent with time as data and processing results from the "OBJECT LEARN" stage are stored in various databases. In general, "OBJECT LEARN," as with any of the learning stage, requires interactive processing with end user participation in which the end user participates by providing input at the object level of abstraction. Then, the system takes over and creates individual object-level databases, which are then concatenated to form local or global object-level databases for use with the "OBJECT CLASSIFY" option 1608, which is automated and requires little end user participation. The "OBJECT LEARN" 1606 option will now be discussed in greater detail.

In "OBJECT LEARN" 1606 under the object processing protocol 1600, the user inspects the labeled image from the pixel or subimage processing protocol 1610. Upon inspection of the image the user will make one or more selections 1612. If the user is satisfied with the results from pixel or subimage processing, then no ROI selections will be made and the object processing protocol will automatically assign all of the ROIs appearing on the labeled image for the application at hand such as segmentation 1614. For example, all the labeled ROIs of the labeled image space will be assigned for laser capture microdissection by the processor and the LCM device will be directed by the processor to execute system functions to extract the ROIs from the tissue sample. If the user selects at least one ROI using a mouse or some other pointing device coupled to the computer, the GUI control will prompt the user at 1616 whether a selection of at least one non-ROI is also desired. A selection of a non-ROI includes selecting a ROI-labeled region that is a false-accept using a mouse or some other pointing device coupled to the computer. A selection of a non-ROI region is a region that is mistakenly labeled as a ROI by the previous subimage or pixel processing protocol but in reality is discerned by the user to be clutter, background or basically a non-ROI. If the user does not select any non-ROIs, then the object processing protocol will automatically assign all of the ROIs appearing on the labeled image at 1618 for the application at hand such as segmentation. For example, all the ROIs will be assigned for laser capture microdissection by the processor and the LCM device will be directed by the processor to execute system functions to extract the ROIs from the tissue sample. If the user selects at least one non-ROI at 1616, then the object processing protocol under "OBJECT LEARN" will commence run classification 1620. The non-ROI selection by the user will constitute an input and stored in an object data file as a non-ROI array that associates a particular labeled region as a false-alarm. Also, a ROI selection by the user will constitute an input and stored in the same object-level data file as a ROI array that associates a particular labeled region as an object ROI. Once an object ROI is designated on the image, that designation is indicated in a color that is different from an object level non-ROI designation on the same image for easy user identification.

With the object-level selections, the object data file is annotated with the additional information obtained from the object level selections. Each object-level selection creates an object-level ROI membership array and an object-level, non-ROI membership array also called a false-alarm membership array, both of which are stored with the associated object data file as input.

Figure 17:
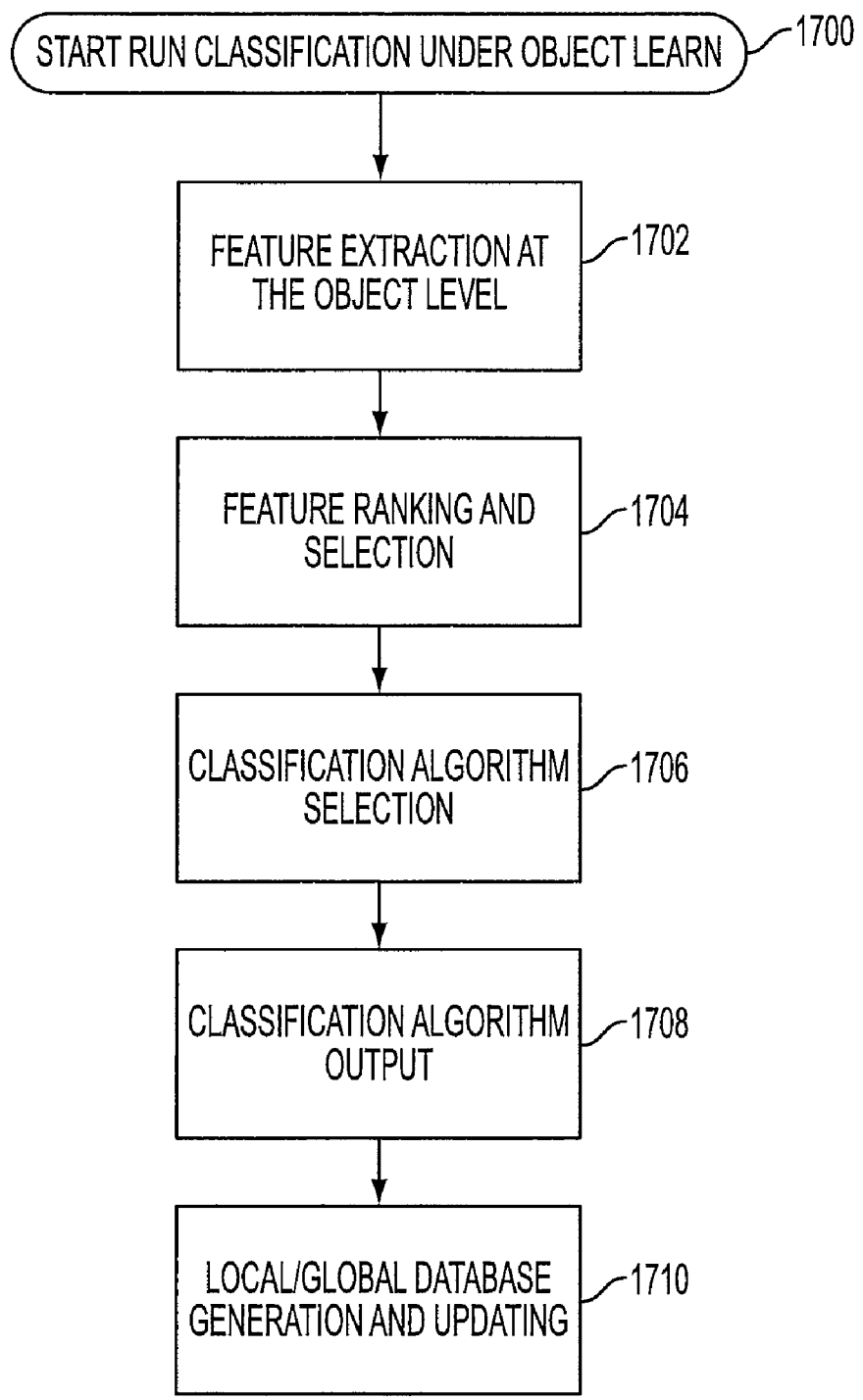
FIG. 17 is a block diagram representation of one method of run-classification under the "OBJECT LEARN" processing option according to the invention.

The next step is to run the classification 1620. Referring now to FIG. 17, there is depicted the steps comprising run classification 1620 in object processing under the "OBJECT LEARN" option 1606. At the start of run classification 1700, the first step is feature extraction 1702 at the object level. Feature extraction 1702 at the object level extracts features that are different from the features extracted at the pixel or subimage level. The following table lists the types of features that are extracted at the object level.

| | TABLE OF OBJECT-LEVEL FEATURES |
|---|---|
| 1 | Major axis length |
| 2 | Minor axis length |
| 3 | Orientation: the angle between the x-axis and the major axis length |
| 4 | Solidity: the fraction of pixels in the object convex hull that are also in the object |
| 5 | Eccentricity (e): The ratio of the distance between the foci to the major axis length (e = 0 if a circle, e = 1 if a line) |
| 6 | Filled area: size of an object |
| 7 | Euler number: Euler number of a binary image for each ROI based on William Pratt's book titled Pratt, William K., Digital Image Processing, New York: John Wiley & Sons, Inc., 1991. p. 633, and incorporated herein by reference in its entirety. |
| 8 | Extent: similar to solidity, except using a bounded box, not a convex hull |
| 9 | Equivalent diameter: diameter (2 r) of a circle, where filled area = 4 $\pi r^2$ |
| 10 | Global texture (3): standard deviation alone |
| 11 | Difference texture (6): similar in concept to subimage processing (standard deviation alone) |
| 12 | Gradient features (2): compute a distance set between centroid and boundary pixels at 45-degree increments |

The features are extracted from the image, compiled in vector form and stored with the associated object data file. The next step is feature ranking and selection 1704 in which the object-level features are ranked according to their effectiveness in discriminating ROIs. Feature ranking is performed in the same way as in pixel and subimage processing by using any combinatorial optimization algorithm known in the art such to first iteratively rank each single object-level feature (singlet) from best feature to worst feature. Feature performance is based on the degree of successful detection of a ROI-annotated region that is made by the user and reserved for performance testing. For example, if a user selects four ROI object-level regions, two ROI selections will be reserved to test the performance of features obtained from the other two ROI selections. Each singlet will be then ranked accordingly using the combinatorial optimization algorithm.

The combinatorial optimization algorithm proceeds to then iteratively rank pairs of features (doublets). For example, the first ranked singlet will be paired with another feature and the performance of both features in combination will be ranked against other doublets. The combinatorial optimization algorithm proceeds to then iteratively rank sets of three features (triplets). For example, the first ranked doublet will be combined with another feature to form a triplet of features, which will be ranked against other triplets. The algorithm ranks singlets, doublets, triplets, quadruplets and so on until the improvement in performance for detecting a ROI reaches a predetermined value or point of diminishing returns at which point a feature singlet, doublet or triplet is extracted. For example, the highest ranked triplet may provide only a small percent increase in performance over the highest ranked doublet in which case, the doublet would be the extracted feature combination to be employed in the next step in classification. This estimation of the point of diminishing returns advantageously enhances real-world performance by avoiding data-overfitting or memorization during learning. The result of the optimization algorithm is an object-level feature subset e.g. a singlet, doublet, or triplet optimal feature selection also called the optimal object-level feature subset (x). The optimal object-level feature subset (x) is stored in the object-level data file. The data file may be any of a number of local or global databases.

The next step is the selection of the classification algorithm 1706 in which an appropriate mapping function is selected that transforms the optimal object-level feature subset (x) into a discrete class label (y). The mapping function is implemented in the form of a classifier. Classification algorithm selection 1706 is performed in the same way as in pixel and object processing. Selection of the classification algorithm 1706 is performed automatically or manually. The user may select a classification algorithm manually from a GUI interface that provides a list of any number of suitable algorithms. Typically, the selection involves a choice between GMM and MVG. Alternatively, automatic selection of the classification algorithm is data dependent and involves a recommendation engine. The recommendation engine is an algorithm that examines the object feature distribution and recommends the MVG classifier for unimodal feature distributions and the GMM classifier if the feature distribution is multimodal. If the actual feature distribution looks multi-modal, GMM is the preferred classifier and the number of clusters determines the number of Gaussian mixtures to be used in representing each class conditional feature distribution. If the actual feature distribution looks unimodal, MVG is the preferred classifier. The recommendation engine also estimates the most appropriate number of modes for the GMM classifier.

As can be seen from above, there are several inputs for the "OBJECT LEARN" processing option, which will now be summarized. The inputs include the image file, which is typically a .jpg or .tif file type, and the labeled image from pixel or subimage processing. Another input is the ROI-membership array for identifying pixel locations and their corresponding classification indices selected manually by the user for all of the pixels in each object level selection. Another input is a non-ROI or false alarm membership array. Another input includes various processing parameters. These processing parameters are stored in a 1×5 row vector wherein the first parameter is the classifier selection. For example, if the user manually inputs or if the recommendation engine automatically selects MVG as the classifier of choice, the second parameter will include a classifier identification such as "1"

for MVG and "2" for GMM. The second parameter is a classifier parameter. This classifier parameter is dependent on the type of classifier selected. For example, for the MVG classifier, the LLR offset is the fourth parameter input where a positive LLR favors ROI detection. For the GMM classifier, the fourth parameter input is the number of Gaussian mixtures. The third and last element in the processing parameters is a flag that is reserved for debugging statements. For example, if this parameter is set to "1", then debug statements will be written to a text file. Of course, another input is a file name, which is used to concatenate object learn data for particular tissue types for example. The file name input includes both path and file name.

Figure 18:
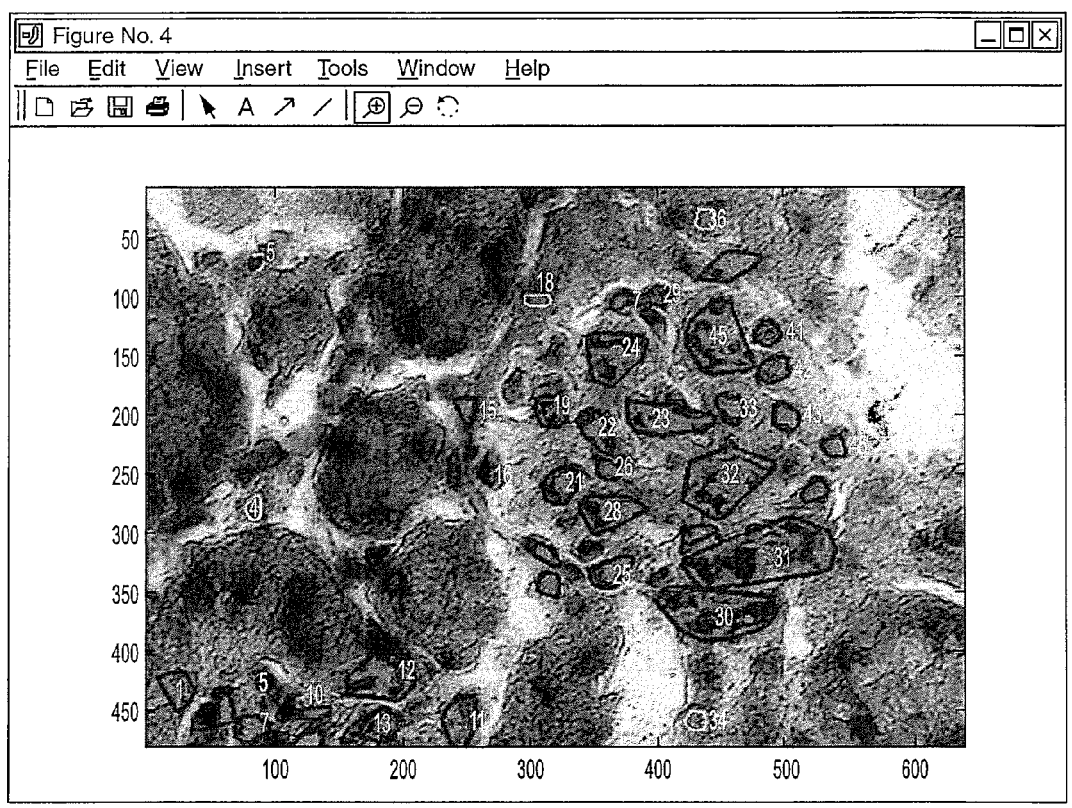
FIG. 18 is one example of a visual output of object processing according to the invention.

The output 1708 of "OBJECT LEARN" processing is a binary object-level map for a two-class problem ("1" for non-ROI and "2" for ROI) that is displayed on the computer monitor for user inspection. The output also provides region labeling in which connected pixels of the same class are aggregated into a region and labeled as a ROI or non-ROI region. Each region is numbered and the region label and number are stored in one or more databases. The labeling can be performed in a variety of ways, and color is used to denote a region identification number for easy user identification of regions. FIG. 18 shows the results of object processing.

The output of the "OBJECT LEARN" processing option is stored in a local object-level database. The output of "OBJECT LEARN" includes the original image, a further refined and labeled image, a boundary structure summarizing classification results, and any error message that may be applicable. The boundary structure that summarizes classification results consists of several fields including a list of pixel locations (x, y) and their corresponding classification, an interior flag, the region area in pixels, the length of the perimeter of a region and the number of boundary pixels. The interior flag is set to one (1) if the boundary of a region belongs to the interior of an object and set to zero (0) otherwise. The list of pixel locations may be sorted, for example by region and by classification.

Database creation and management 1710 is the same as that discussed above with respect to pixel processing and described in FIG. 9 with the word "pixel" being replaced with the word "object." As shown in FIG. 4, object processing 410 is in electrical communication with various local and global databases 414. As additional ROI and non-ROI selections are made by the user when in the "OBJECT LEARN" processing protocol, the optimal object-level feature subset (x) is re-compiled for the entire data file either local or global. Any local and global database to which object processing results are concatenated also undergoes the combinatorial optimization algorithm for a refinement of the resident optimal object level feature subset.

The "OBJECT CLASSIFY" option will now be discussed. "OBJECT CLASSIFY" employs data accumulated and stored in various databases from one or more learning stages such as the "OBJECT LEARN" stage. As discussed above, during "OBJECT LEARN" the user provides truth annotations, for example ROI and non-ROI object-level selections for representative images using GUI controls. Then, the system discriminates ROIs from non-ROIs using classifiers. During the learning stage, all the parameters and feature values associated with pattern learning are stored for each image being investigated in one or more database such as local and global databases. The data from "OBJECT LEARN" is also concatenated to one or more global databases as discussed above. During "OBJECT CLASSIFY" the system utilizes the learned parameters stored in one or more databases to perform automatic classification of regions as being ROIs or non-ROIs. As the databases grow with time as more data is acquired during "OBJECT LEARN," "OBJECT CLASSIFY" improves with age. The "OBJECT CLASSIFY" operating mode is designed for high-throughput batch processing with the human operator inspecting the processed results for final decision.

Referring back to FIG. 16, after "OBJECT CLASSIFY" is selected as the object processing option at 1604, "SUBIMAGE CLASSIFY" will start 1608 by prompting the user via the GUI to load an appropriate database 1622 if one is available. If no appropriate database is available, the user will be directed to start "OBJECT LEARN" 1606. A pull-down menu on the GUI provides a list of appropriate local and global databases to be selected by the user under "OBJECT CLASSIFY" and the user selects an object-level database 1624. Typically, the available databases are ones created during "OBJECT LEARN" and matched for the particular image at hand. For example, if the image is a pancreatic tissue sample, the user may select any local or global pancreatic tissue database created at the object level. The next step is to run the classification 1626.

Figure 19:
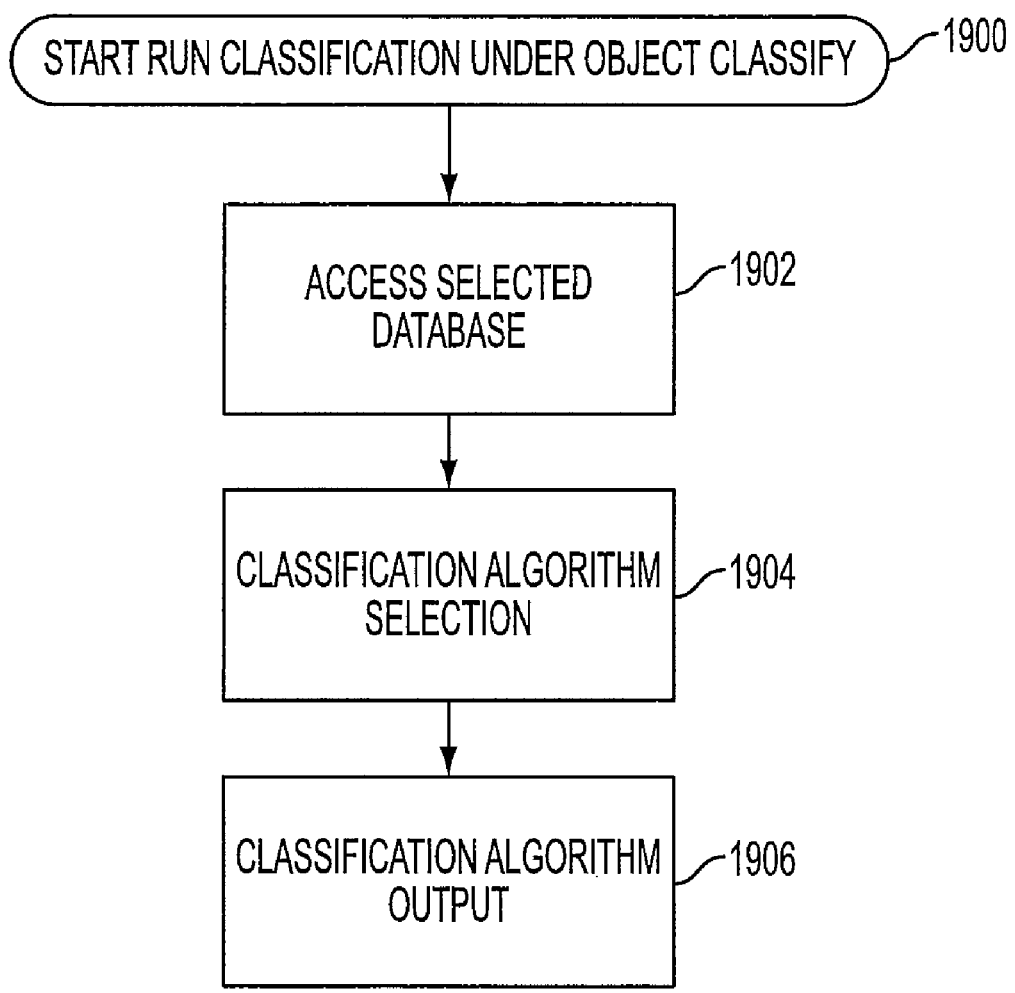
FIG. 19 is a block diagram representation of one method of run-classification under the "OBJECT CLASSIFY" processing option according to the invention.

Running the classification under "OBJECT CLASSIFY" is depicted in FIG. 19. After the start of "run classification" 1900, the database that was selected at 1624 is accessed 1902 for its critical algorithmic parameters and for the optimal object feature subset. The critical algorithmic parameters are inputted along with the image and labeled image from pixel or subimage processing. The selected object-level database has already been updated at 1710 for example. Hence, the database has undergone a ranking or re-ranking of features and selection or re-selection of the optimal object-level feature subset with each additional input of information. Therefore, these values are ready for use with the classification algorithm that is selected at 1904.

In "OBJECT CLASSIFY," the classification algorithm is selected automatically. Automatic selection of the classification algorithm is data dependent and involves a recommendation engine. The recommendation engine is an algorithm that examines the feature distribution and recommends the MVG classifier for unimodal object-level feature distributions and the GMM classifier if the object-level feature distributions are multimodal. The recommendation engine also estimates the most appropriate number of modes for the GMM classifier.

The output of "OBJECT CLASSIFY" is a binary image map for the two-class problem ("1" for non-ROI and "2" for ROI) that is displayed on the computer monitor for user inspection. The output also provides region labeling in which connected pixels of the same class are aggregated into a region and labeled as an object level ROI or non-ROI region. Each region is numbered and the region label and number are stored in one or more databases as shown in FIG. 18. The labeling can be performed in a variety of ways, and color is used to denote a region identification number for easy user identification of regions.

The output 1906 of "OBJECT CLASSIFY" includes the original image, the labeled image, a boundary structure summarizing classification results, and any error message that may be applicable. The boundary structure that summarizes classification results consists of several fields including a list of pixel locations (x, y), an interior flag, the region area in pixels, the length of the perimeter of a region and the number of boundary pixels. The interior flag is set to one (1) if the boundary of a region belongs to the interior of an object and set to zero (0) otherwise. The list of pixel locations may be sorted, for example by region and by classification. The output is stored in a local or global database.

Upon viewing the output of either the "OBJECT LEARN" or "OBJECT CLASSIFY" options, the user determines that the output binary image map is satisfactory and manually selects from the GUI to proceed with LCM immediately or at a later time. Alternatively, the processor may directly proceed with LCM without selection from the GUI. If the tissue slide is loaded in the LCM device, the processor will automatically position the laser at coordinates corresponding to ROIs from the binary image map. Once positioned, the laser is activated for LCM and the ROIs are automatically transferred to the LCM transfer film and removed from the tissue sample.

Figure 20:
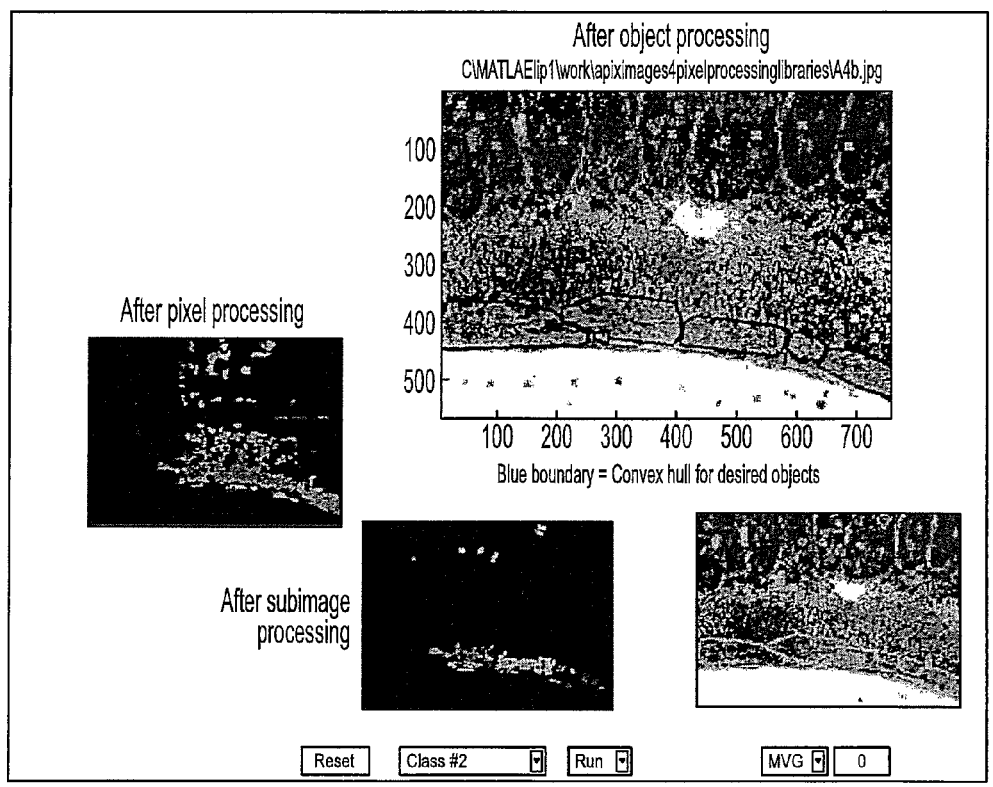
FIG. 20 is one example of a visual output of the image, the image after pixel processing, the image after subimage processing and the image after object processing.

FIG. 20 shows the improving performance of tissue recognition as the abstraction protocol proceeds from pixel to subimage to object processing. After pixel processing, a lot of unwanted regions above the epithelial layer still remain. However, with subimage and object processing that utilize features at a higher level of abstraction, almost all of the false detected regions are filtered out, thereby greatly improving the accuracy of extracting the right tissues using LCM equipment While the present invention has been described with reference to one or more particular variations, those skilled in the art will recognize that many changes may be made thereto without departing from the spirit and scope of the present invention. Each of these embodiments and obvious various thereof are contemplated as falling within the spirit and scope of the claimed invention, which is set forth in the claims.

The invention claimed is:

1. A method for image analysis, the method comprising:
receiving a first image at a processor;
transforming the first image into a feature space;
selecting a region of interest (ROI) at a pixel level of processing from the first image, wherein the ROI is a portion of the first image;
extracting two or more features from the ROI at a pixel level of processing;
selecting a non-ROI at a pixel level of processing from the first image, wherein the non-ROI is a portion of the first image and independent of the selected ROI;
extracting two or more features from the non-ROI at a pixel level of processing;
ranking, in a combinatorial manner, the extracted features from the ROI and the non-ROI based on feature performance for successful detection of a selected ROI at a pixel level of processing;
recording the ranked extracted features;
selecting a classification algorithm;
running the classification algorithm to classify the first image or a second image into one or more ROIs at a pixel level of processing based in part on comparing the selected ROI and non-ROI, wherein the first or second image selected for classification is a classified image;
determining a size of one or more of the ROIs based on pixel level processing; and
outputting analysis results to a computing device.

2. The method of claim 1, wherein selecting at least one ROI comprises selecting one or more pixels from the image; and wherein the step of selecting at least one non-ROI comprises selecting one or more pixels from the image.

3. The method of claim 1, further comprising transmitting the recorded ROIs at a pixel level of processing for laser capture microdissection.

4. The method of claim 1, further comprising selecting a second level of processing.

5. The method of claim 4, wherein the second level of processing is subimage level processing.

6. The method of claim 5, further comprising the steps of:
selecting at least one polygonal ROI from the classified image at a subimage level of processing;
extracting one or more features from the polygonal ROI at a subimage level of processing;
selecting at least one polygonal non-ROI at a subimage level of processing;
extracting one or more features from the non-ROI at a subimage level of processing;
ranking the extracted features based on feature performance for successful detection of a selected ROI;
recording the ranked features based on subimage processing;
selecting a classification algorithm;
running the classification algorithm to classify the image into ROIs based on subimage level processing; and
recording the ROIs based on subimage level processing.

7. The method of claim 6, further comprising transmitting the recorded regions of interest based on subimage level processing for laser capture microdissection.

8. The method of claim 4, wherein the second level of processing is object processing.

9. The method of claim 8, further comprising:
selecting at least one polygonal ROI from the classified image at an object level of processing.

10. The method of claim 9, further comprising:
recording the at least one polygonal ROI at object level of processing; and
transmitting the at least one polygonal region of interest based on object level processing for laser capture microdissection.

11. The method of claim 9, further comprising:
extracting one or more features from the ROI at an object level of processing;
selecting at least one polygonal non-ROI at an object level of processing;
extracting one or more features from the non-ROI at an object level of processing;
ranking the extracted features based on feature performance for successful detection of a selected ROI;
recording the ranked features based on object level processing;
selecting a classification algorithm;
running the classification algorithm to classify the image into ROIs based on object level processing; and
recording the ROIs based on object level processing.

12. The method of claim 11, further comprising transmitting the ROIs based on object level processing for laser capture microdissection.

13. The method of claim 4, further comprising selecting a third level of processing.

14. The method of claim 13, wherein the third level of processing is object level processing.

15. The method of claim 14, further comprising:
selecting at least one polygonal ROI from the classified image at an object level of processing.

16. The method of claim 15, further comprising:
recording the at least one polygonal ROI at an object level of processing;
transmitting the at least one polygonal ROIs based on object level processing for laser capture microdissection.

17. The method of claim 15, further comprising:
extracting one or more features from the ROI at an object level of processing;
selecting at least one polygonal non-ROI at an object level of processing;

extracting one or more features from the non-ROI at the object level of processing;

ranking the extracted features based on feature performance for successful detection of a selected ROI;

recording the ranked extracted features based on object level processing;

selecting a classification algorithm;

running the classification algorithm to classify the image into ROIs based on object level processing; and recording the ROIs based on object level processing.

18. The method of claim 17, further comprising transmitting the regions of interest based on object level processing for laser capture microdissection.

19. The method of claim 6, wherein the further steps are performed prior to outputting the analysis results.

20. The method of claim 6, wherein the further steps are performed after outputting the analysis results, and wherein the method further comprises outputting the analysis results after performing the further steps.

21. The method of claim 11, wherein the further steps are performed prior to outputting the analysis results.

22. The method of claim 11, wherein the further steps are performed after outputting the analysis results, and wherein the method further comprises outputting the analysis results after performing the further steps.

23. The method of claim 17, wherein the further steps are performed prior to outputting the analysis results.

24. The method of claim 17, wherein the further steps are performed after outputting the analysis results, and wherein the method further comprises outputting the analysis results after performing the further steps.

25. The method of claim 1, wherein ranking comprises first iteratively ordering each individual feature for a given ROI or non-ROI according to ability of the single feature to detect an ROI and then iteratively ordering pairs of features for a given ROI or non-ROI according to ability of the pair of features to detect an ROI.

* * * * *